United States Patent [19]

Davison et al.

[11] Patent Number: 4,673,562

[45] Date of Patent: Jun. 16, 1987

[54] BISAMIDE BISTHIOL COMPOUNDS USEFUL FOR MAKING TECHNETIUM RADIODIAGNOSTIC RENAL AGENTS

[75] Inventors: Alan Davison, Needham; David Brenner; John Lister-James, both of Cambridge; Alun G. Jones, Newton Centre, all of Mass.

[73] Assignees: The Children's Medical Center Corporation, Boston; Massachusetts Institute of Technology, Cambridge, both of Mass.

[21] Appl. No.: 524,888

[22] Filed: Aug. 19, 1983

[51] Int. Cl.[4] .................. A61K 43/00; A61N 5/12; C07F 13/00

[52] U.S. Cl. .................. 424/1.1; 556/14; 564/159

[58] Field of Search .......... 260/429 R; 424/1.1; 534/14; 564/159

[56] References Cited

U.S. PATENT DOCUMENTS

| | | | |
|---|---|---|---|
| 3,466,361 | 9/1969 | Richards | 260/429 R X |
| 3,873,680 | 3/1975 | Jackson et al. | 268/429 R X |
| 3,928,552 | 12/1975 | Winchell et al. | 260/429 R |
| 3,981,980 | 9/1976 | Baker et al. | 260/429 R X |
| 3,987,157 | 10/1976 | Molinski et al. | 260/429 R X |
| 3,989,730 | 11/1976 | Subramanian et al. | 260/429 R X |
| 4,017,596 | 4/1977 | Loberg et al. | 260/429 R X |
| 4,031,198 | 6/1977 | Jackson et al. | 424/1.1 |
| 4,054,645 | 10/1977 | Hill et al. | 260/429 R X |
| 4,057,615 | 11/1977 | Bardy et al. | 260/429 R X |
| 4,208,398 | 6/1980 | Kubiatowicz et al. | 424/1.1 |
| 4,233,285 | 11/1980 | Winchell et al. | 424/1.1 |
| 4,316,883 | 2/1982 | Schrijver | 260/429 R X |
| 4,418,208 | 11/1983 | Nunn et al. | 424/1.1 |
| 4,444,690 | 4/1984 | Fritzberg | 260/429 S |
| 4,452,774 | 6/1984 | Jones et al. | 260/429 R X |

OTHER PUBLICATIONS

Chemical Abstracts, 83, 120919s (1975).
Chemical Abstracts, 83, 120920k (1975).
Chemical Abstracts, 90, 109930n (1979).
Chemical Abstracts, 90, 109931p (1979).
Chemical Abstracts, 93, 128054h (1980).
Chemical Abstracts, 93, 102019a (1980).
"Radiopharmaceuticals for Quantitative Study of Renal Function", M. D. Blaufox et al., Radiopharmaceuticals #41, pp. 385-392.
"Chemical and In Vivo Studies of the Anion Oxo[N,-N'-ethylenebis(2-Mercaptoacetimido)]Technetate (V)", A. Jones et al., J. Nucl. Med., vol. 23, No. 9, pp. 801-809 (Sep. 1982).
"Synthesis and Biological Evaluation of Tc-99mN,-N'-Bis(Mercaptoacetyl)-2,3-Diaminopropanoate: A Potential Replacement for [131I]o–Iodohippurate", J. Nucl. Med., vol. 23, No. 7, pp. 592-598 (A. Fritzberg et al) (1982).
"Chemical and Biological Studies of Tc-99m N,N'-Bis(Mercaptoacetamido)Ethylenediamine: A Potential Replacement for 1-131 Iodohippurate", A. Fritzberg et al., J. Nucl. Med., vol. 22, No. 3, pp. 258-263 (1981).
"Renal Clearance and Extraction Parameters of Ortho-Iodohippurate (1-123) Compared with OIH(1-131) and PAH", R. Stadainik et al., J. Nucl. Med., vol. #21, pp. 168-170 (1980).
"The Investigation of Radiopharmaceutical Components by Fast Atom Bombardment Mass Spectrometry: The Identification of Tc-HIDA and the Epimers to Tc–CO$_2$DADS", Costello et al., J. Nucl. Med., vol. 24, #4, pp. 353-355 (1983).
"A New Class of Oxotechnetium(5+) Chelate Complexes Containing a TcON$_2$S$_2$ Core", A. Davison et al., Inorganic Chemistry, vol. 20, No. 6, pp. 1629-1632 (Jun. 1981).
"Evaluation of Glomerular Filtration Rate with 99m Tc-DTPA", H. Atkins et al, J. Nucl. Med., vol. 12, p. 338 (1971).
"Radiopharmaceuticals in Evaluation of Kidneys", Winchell, Int. Symposium Radiopharmaceutical, II, pp. 459-463 (1979).
"Preparation and Use of I$^{131}$ Labeled Sodium Iodohippurate in Kidney Function Tests", Tubis et al., Proc. Soc. Exp. Biol. Med., 103, pp. 497-498 (1960).
"Use of Radioiodinated Hippuran for Individual Kidney Function Tests", Nordyke et al., J. Lab. Clin. Med., pp. 438-445, vol. 56, No. 3, (Sep. 1960).
"The Preparation of a Known Technetium Complex with a Variety of Reducing Agents", C. Orvig et al., J. Nucl. Med., vol. 20, No. 6, p. 653 (1979).
"A Series of Oxotechnetium(+5) Chelate Complexes Containing a TcOS$_2$N$_2$ Core", Davison et al., J. Nucl. Med., vol. 22, No. 6, (1981) pp. 57-58.
"A New Type of Oxotechnetium (V) Complex", DePamphilis et al., Proc. 3rd International Symposium Radiopharmaceutical Chem., pp. 146-147, Jun. 1980.
"A Tetradentate Ligand Designed Specifically to Coordinate Technetium", A. Davison et al., J. Nucl. Med., vol. 20, No. 6, p. 641 (1979).
"Oxotechnetium Complexes Containing TcOn$_2$S$_2$ Cores", A. Jones et al., Fourth International Symposium on Radiopharmaceutical Chemistry, p. 333, Aug. 23-27, 1982.
"Hepatobiliary Transport Mechanism of Tc-99m-N,a-(2,6-Diethylacetanilide)Iminodiacarboxylic Acid (Diethyl-IDA)", Fritzberg et al., J. Nucl. Med., vol. 20, No. 6, p. 642 (1979).

(List continued on next page.)

*Primary Examiner*—Helen M. S. Sneed

[57] ABSTRACT

A radiodiagnostic bisamido-bisthio ligand useful for producing Tc-labelled radiodiagnostic renal agents is described. The ligand forms a complex with the radionuclide $^{99m}$Tc suitable for administration as a radiopharmaceutical to obtain images of the kidney for diagnosis of kidney disfunction.

45 Claims, No Drawings

OTHER PUBLICATIONS

"Tc-99m Complexes Based on Diamide Dimercaptide Donor Groups ($N_2S_2$) as Potential Renal Function Agents", Fritzberg et al., J. Nucl. Med., vol. 23, #5, p. 17 (1982).

"Chemical and Biological Studies of Tc-99m-N,N'-Bis(Mercaptoacetamido) Ethylenediamine: A Potenital Replacement for I-131-Hippuran", Fritzberg et al., J. Nucl. Med., vol. 22, #6, p. 52 (1981).

"Renal Transport Mechanism Studies of Tc-99m-N,n'-Bis-(Mercaptoacetamido) Ethylenediamine", Fritzberg et al, J. Nucl. Med., vol. 22, #6, p. 51, (1981).

"Clinical Comparison of Tc-99m-N,N-Bis(Mercaptoacetamido)Ethylenediamine (Tc-DADS) and I-131-Hippuran (I-H) for Evaluation of Renal Tubular Function", Klingensmith et al., J. Nucl. Med., vol. 22, #6, p. 38, (1981).

"Clinical Evaluation of Tc-99m,N,N'-Bis(Mercaptioacetyl)2,3-Diaminopropanoate (Component A) (Tc-99m-$CO_2$-DADS-A) as a Replacement for I-131-Hippuran", Klingensmith et al., J. Nucl. Med., vol. 24, No. 5, p. 80 (1983).

"Technetium-99m Bifunctional Chelating Agent-Thiolactone for Coupling to Biomolecules, $N_2S_2$ Ligand for Chelation to Technetium," Byrne et al., Society of Nuc. Med. 30th Annual Meeting, Jun. 7-10, 1983.

"An Evaluation of 16 New Tc-99m Compounds for Renal Tubular Excretion Studies", Subramanian et al., J. Nucl. Med., vol. 24, No. 5, p. 80 (1983).

BISAMIDE BISTHIOL COMPOUNDS USEFUL FOR MAKING TECHNETIUM RADIODIAGNOSTIC RENAL AGENTS

This invention was made with government support and the U.S. government has certain rights in the invention.

FIELD OF THE INVENTION

The present invention relates to radiodiagnostic agents and, more particularly, to ligands useful as intermediates for producing $^{99m}$Tc-labelled radiodiagnostic agents, novel $^{99m}$Tc-labelled radiodiagnostic agents, kits for preparing such $^{99m}$Tc-labelled radiodiagnostic agents and the methods for using such $^{99m}$Tc-labelled radiodiagnostic agents.

BACKGROUND OF THE INVENTION

Clinical nuclear medicine tests of renal perfusion and excretion using radioactive compounds are a widely used and valuable technique for diagnosing kidney disfunction. Chronic renal disease and associated renal failure today constitute a major endemic medical problem with a serious impact on health costs. Thus, the clinical assessment of renal problems using such noninvasive radionuclide procedures and, in particular, methods for early diagnosis and evaluation of renal function prior to and after therapeutic intervention have achieved general recognition in the past few years.

Although renal structure can be determined in great detail using radiography, ultrasound, and x-ray computed tomography, the critically important functional evaluation of renal disease with these modalities is not as accurate as with radionuclide techniques. Moreover, the principal virtue of the latter is not only their accuracy, but also the speed with which they can be performed, employing a noninvasive methodology with minimum discomfort to the patient and a relatively low radiation dose to pediatric as well as adult patients. In serial monitoring, such factors assume a great degree of significance.

The most important aspects of kidney function to which radionuclide procedures are applied are the estimation of glomerular filtration and of tubular function. The ligands and their corresponding Tc-99m complexes which are the subject of this invention are useful as diagnostic agents for the study of tubular secretion and, hence, renal plasma flow.

Renal plasma flow is an important parameter of kidney function that is determined by the clearance of a compound which is nearly completely extracted from the renal blood, ideally in a single transit. In practice, the measurements fall below the true renal plasma flow, because the compounds previously used do not have this property. Thus, the term effective renal plasma flow (ERPF) has come into existence. Apart from being almost completely extracted in a short period of time, the other principal requirements of such a renal diagnostic compound are that it should be rapidly excreted unchanged, that it not be extensively metabolized, and that there be no significant extrarenal pathway of excretion.

Initially, radioiodinated iodo-pyracet (Diotrast TM) was used for the measurement of ERPF, but its partial removal from the circulation by the liver necessitated complicated methods of quantification as well as critical probe manipulation in order to view the kidneys and exclude hepatic radioactivity. Subsequently, such radiopharmaceuticals such as Hypaque TM sodium and Renografin TM were introduced because they were not appreciably removed from circulation by the liver. Thus, a probe could be placed at the right angle to the back with relatively wide collimation and without X-ray localization of the liver. Although these substances were an improvement over Diodrast TM, they had the disadvantage of being removed from the blood much more slowly than Diodrast TM which prolonged test time and decreased the effective ability of detection of kidney function differences.

Paraaminohippuric acid (PAH) is currently the compound of choice for chemical (i.e. nonradioactive) estimation of ERPF, and is generally regarded as a reference. PAH is eliminated by the kidneys partially by glomerular filtration (20%) and partially by tubular secretion (80%). Its extraction by the normal kidney is 90%, with the rest being returned by the general circulation. Because chemical analysis of PAH in blood and urine samples is cumbersome, however, this presents a disadvantage with respect to its widespread use. Additionally, this key material is not available as a radiopharmaceutical labelled with a gamma-emitting radionuclide suitable for external visualization using gamma scintillation cameras.

A related compound $^{131}$I-ortho-iodohippurate (Hippuran TM or OIH), available typically as the sodium salt, was found to have a lower clearance than PAH. Nevertheless, OIH has found use as a radiodiagnostic renal agent for ERPF measurements. The uptake in normal kidneys following a bolus injection is rapid, reaching a maximum within the first five minutes and, in a normally hydrated patient, will clear from the renal parenchyma and collecting system within thirty minutes. At that point, approximately 70% of the injected dose can be found in the urine. It is known, however, that this figure can vary significantly both with the state of hydration of the patient and with the disease.

A disadvantage of OIH is that the physical decay characteristics of the radionuclide $^{131}$I preclude the administration of a sufficient amount of activity to effectively study the initial perfusion of the organ after a bolus injection of the radiopharmaceutical. Despite the favorable pharmacokinetics and low background activity, the statistical accuracy of the measurements may therefore be reduced below the point where they are deemed useful. Furthermore, the principal gamma ray emitted by the radioactive label (364 keV) is higher than optimal for current detector designs, and the resolution of the image during this first phase of the renogram is poor.

Another radiopharmaceutical ($^{99m}$Tc-DTPA) is now often used as an alternative to determine renal perfusion. This complex is formed when $^{99m}$Tc pertechnetate is reduced in the presence of diethylenetriamine pentaacetic acid (DTPA). Because this complex is excreted exclusively by glomerular filtration, however, the images obtained can be poor in cases where the renal function is compromised. This is principally because in the normal adult glomerular filtration rate is approximately 120 ml/minute wherein the renal plasma flow as measured by PAH is about 575 ml/minute.

In practice, therefore, a compound labelled with $^{99m}$Tc and which is extracted efficiently by the kidney could effectively supplant both OIH and $^{99m}$Tc-DTPA, the existing agents of choice. The use of a simple radiopharmaceutical of this type would greatly decrease the duration of the test, the reagents required, and also the cost.

The radionuclide $^{99m}$Tc has excellent physical decay characteristics for application in nuclear medicine, and is readily available in a radionuclide generator system. More than 80% of all diagnostic nuclear medicine procedures in the United States now involve the administration of radiopharmaceuticals labelled with this radioisotope. The 140 keV gamma ray emitted in 89% of all disintegrations of this metastable nuclear state is well matched to the properties of modern scintillation camera systems, and the level of nonpenetrating radiation following decay gives a low absorbed radiation dose to the recipient. In turn, this means that large amounts of radioactivity can be administered leading to more reliable statistics in quantitative studies. Thus, serial monitoring also is possible with technetium. Additionally, the halflife of 6.02 hours is better matched to the length of the study than that of $^{131}$I (8 days). In the chemical form of pertechnetate ($^{99m}$TcO$_4^-$), however, its absolute concentration in the renal parenchyma is low and imaging studies have poor resolution. In addition, urinary excretion of pertechnetate is relatively slow, about 86% of the filtered activity being reabsorbed by the renal tubules and, hence, pertechnetate per se cannot be employed efficiently for renal function studies.

Therefore, an agent labelled with $^{99m}$Tc and having a renal extraction comparable to or greater than OIH is highly desirable because it would allow diagnostic information to be obtained from all three portions of the renogram: the vascular (tracer appearance), the tubular reabsorption (blood flow), and the excretion (drainage) phases. The expected clinical applications would include, for example, the screening of hypertensive patients for unilateral renal disease, the detection of obstructive lesions, the early diagnosis of renal transplant rejection, the monitoring of urinary transit, etc. Furthermore, because of the low radiation dose, such studies may be carried out in pediatric patients or during pregnancy.

A bisamide bisthiol (N$_2$S$_2$) chelate that forms a complex with reduced technetium, [$^{99m}$TcO(ema)]$^-$, was described as a potential renal agent by Davison et al *J. Nucl. Med.* 20(60), 641 (1979). It was subsequently shown to be excreted into both the urine and bile in a chemically unchanged form, Jones et al *J. Nucl. Med.* 23(9), 801 (1982), thus fulfilling one of the requirements for a renal agent. Fritzberg evaluated [TcO(ema)]$^-$ in renal transplant patients and found that, although the images were excellent, there were 7 to 10% of the material clearing into bile and this interfered with evaluation of the kidneys in their normal position. Thus, a single agent for determining renal function is still being sought.

SUMMARY OF THE INVENTION

The present invention provides compounds that form complexes with technetium. When these complexes are injected intravenously into a mammal, they are rapidly excreted through the kidney (predominantly via tubular secretion) and provide a visual measure of renal function.

The compounds of the present invention can generally be represented by the structural formulae I and II as follows:

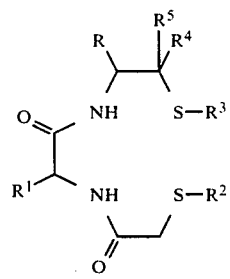

and

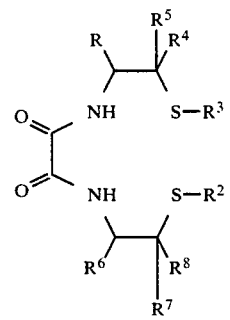

wherein R and $R^6$ are each selected from hydrogen, substituted or unsubstituted lower alkyl or —COR$^9$ where $R^9$ is selected from hydroxy, substituted or unsubstituted lower alkoxy, substituted or unsubstituted amino, glycine ester, or an activated leaving group; $R^1$ is selected from hydrogen, or substituted or unsubstituted lower alkyl; $R^2$ and $R^3$ are each selected from hydrogen or a thiol protecting group; and $R^4$, $R^5$, $R^7$ and $R^8$ are each selected from hydrogen or lower alkyl; and salts thereof.

The compounds of formulas I and II can be complexed with technetium to form the following complexes:

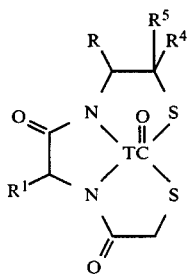

and

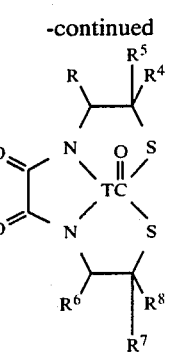

where the R groups are as defined above; and salts thereof.

The present invention also provides kits for producing technetium-99m complexes of the type illustrated by formulas III and IV. The kits typically comprise bisamide-bisthiol compounds of the type illustrated by formulas I and II and a reducing agent for pertechnetate in a sealed, sterilized container. Preferably, the kits comprise lyophilized bisamide-bisthiol compounds containing hydrophilic thiol protecting groups which permit ready reconstitution with aqueous solutions having a pH in the range of 5 to 8.

DETAILED DESCRIPTION OF THE INVENTION

In accord with the present invention, compounds of the type having formulae I and II are useful for preparing technetium complexes of formulae III and IV. These technetium complexes of the present invention are useful as radiodiagnostic agents, particularly for diagnosing abnormalities of kidney function.

In the above formulae, when R or $R^6$ is a carboxylicacid derivative, $R^9$ can be an activated leaving group. For purposes of this invention a leaving group $R^9$ is defined such that [compound]—$COR^9$ is an acylating agent. Examples of activated leaving groups suitable for the practice of this invention include, for example, halide, substituted or unsubstituted aryloxy such as phenoxy, pentachlorophenoxy, etc.; oxy-heterocyclic such as N-oxy-succinimido, etc.; mercapto, lower alkylthio, arylthio, oxyphosphonium, or other groups known to those skilled in the art to be useful as leaving groups.

$R^2$ and $R^3$ can be hydrogen or any known thiol protecting group. Some examples of such groups are lower alkylaminocarbonyl such as ethylaminocarbonyl, lower alkanoylaminomethyl, aroylaminomethyl, t-butyl, acetamidomethyl, arylmethyl such as triphenylmethyl (trityl) and diphenylmethyl, aroyl such as benzoyl, aryloxycarbonyl such as phenoxycarbonyl, aryloweralkoxylcarbonyl, preferably arylmethoxycarbonyl such as benzyloxycarbonyl, and lower alkoxycarbonyl such as t-butoxycarbonyl. Preferred thiol protecting groups include trityl, t-butyl, diphenylmethyl, acetamidomethyl and benzoyl.

The term "lower alkyl" when used in this application designates aliphatic saturated branched or straight chain hydrocarbon monovalent substituents containing from 1 to 4 carbon atoms such as methyl, ethyl, isopropyl, n-propyl, n-butyl, t-butyl, etc. The term "lower alkoxy" designates lower alkoxy substituents containing from 1 to 4 carbon atoms such as methoxy, ethoxy, isopropoxy, etc.

The terms substituted lower alkyl or substituted lower alkoxy when used herein include alkyl and alkoxy groups substituted with halide, hydroxy, carboxylic acid, or carboxamide groups, etc. such as, for example, —$CH_2OH$, —$CH_2CH_2COOH$, —$CH_2CONH_2$, —$OCH_2CH_2OH$, —$OCH_2COOH$, —$OCH_2CH_2CONH_2$, etc.

The term substituted amino when used herein includes such groups mono or di substituted with lower alkyl, and —$NH_3^+$ or mono, di and tri-substituted ammonium groups substituted with lower alkyl with a pharmacologically suitable anion.

The term glycine ester as used herein means the lower alkyl esters of glycine, preferably the methyl and ethyl esters.

Compounds of formula I can be synthesized by the following general reaction scheme.

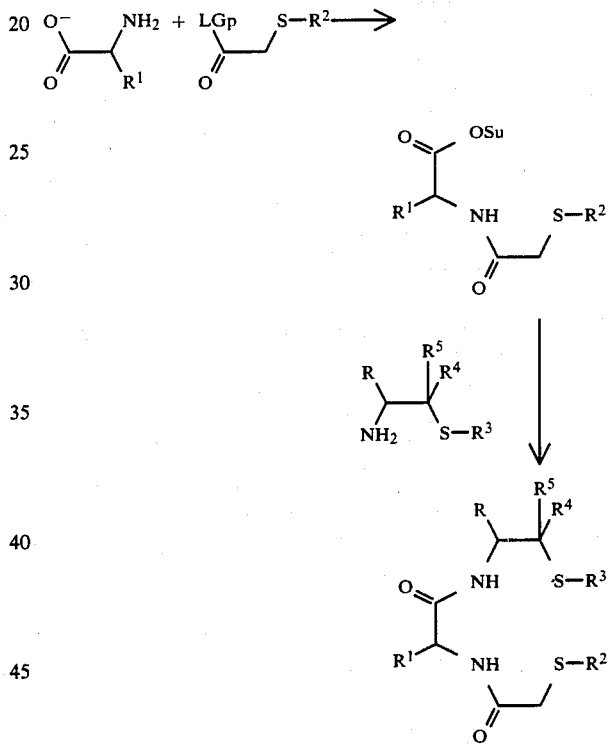

where Su is succinimide, LGp is a leaving group, and the R's are as defined above.

Compounds of formula II can be synthesized by the following general reaction scheme.

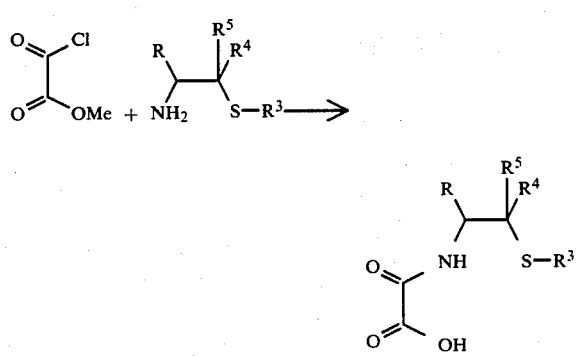

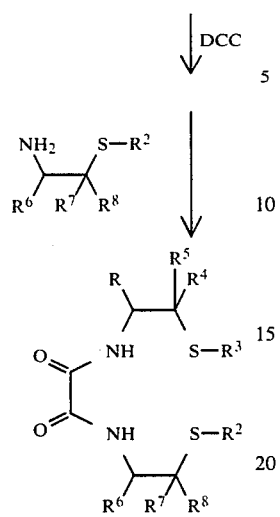

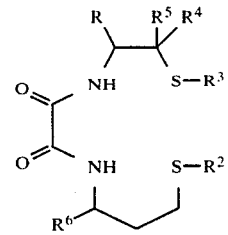
(A)

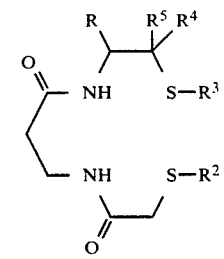
(B)

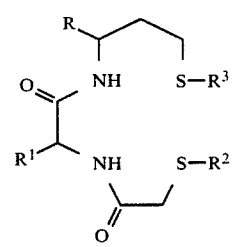
(C)

and

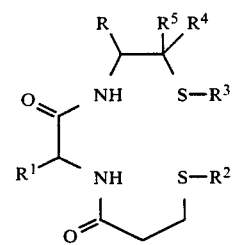
(D)

where the R's are as defined above; and salts thereof.

Examples of compounds of this invention include:
N-(2-mercaptoethyl)-(2-mercaptoacetyl)glycinamide;
N-[2-(benzoylthio)ethyl]-(2-benzoylthioacetyl)glycinamide;
N-[2-(acetamidomethylthio)ethyl]-(2-acetamidomethylthioacetyl)glycinamide;
(2-mercaptoacetyl)glycyl-cysteine methyl ester;
(2-benzoylthioacetyl)glycyl-(S-benzoyl)cysteine methyl ester;
[2-(acetamidomethylthio)acetyl]glycyl-(S-acetamidomethyl)cysteine methyl ester;
(2-mercaptoacetyl)glycyl-cysteine;
(2-benzoylthioacetyl)glycyl-(S-benzoyl)cysteine;
[2-(acetamidomethylthio)acetyl]glycyl-(S-acetamidomethyl)cysteine;
(2-mercaptoacetyl)glycyl-cysteinyl-glycine methyl ester;
(2-benzoylthioacetyl)glycyl-(S-benzoyl)cysteinyl-glycine methyl ester;
[2-(acetamidomethylthio)acetyl]glycyl-(S-acetamidomethyl)cysteinyl-glycine methyl ester;
N-(2-mercaptoethyl)-N'-(1-carbomethoxy-2-mercaptoethyl)oxamide;
N-[2-(benzoylthio)ethyl]-N'-[1-carbomethyoxy-2-(benzoylthio)ethyl]oxamide;
N-[2-(acetamidomethylthio)ethyl]-N'-[1-carbomethoxy-2-(acetamidomethylthio)ethyl]oxamide;
N,N'-bis(2-mercaptoethyl)oxamide;
N,N'-bis[2-(benzoylthio)ethyl]oxamide;
N,N'-bis[2-(acetamidomethylthio)ethyl]oxamide;
(R,R)N,N'-bis(1-carbomethoxy-2-mercaptoethyl)oxamide;
(R,R)N,N'-bis[1-carbomethoxy-2-(benzoylthio)ethyl]oxamide; and
(R,R)N,N'-bis[1-carbomethoxy-2-(acetamidomethylthio)ethyl]-oxamide.

The bisamide-bisthiol compounds of this invention include compounds similar to those illustrated by formulae I and II but having an extra carbon in the carbon bridge between one or more of the pairs of nitrogen and sulfur atoms. When such an extra carbon is added that portion of the compound when complexed with technetium will form a six member ring. Examples of such bisamide-bisthiol compounds include:

where the R's are the same as defined above, and salts thereof. These compounds are readily formed by the same techniques as described above by substituting the appropriate propyl derivative in place of the corresponding ethyl derivative in the reaction scheme. Additional such compounds will be readily apparent to those skilled in the art.

Technetium complexes of this invention are formed by reacting the compounds of formulae I and II with technetium in the presence of a suitable reducing agent in the conventional manner. For example, the compound is dissolved in a suitable solvent with a reducing agent and pertechnetate is added. The mixture is heated for a suitable length of time to complete the reaction. Typically, heating in a boiling water bath for about 10 minutes has been found sufficient to obtain very good yields of the technetium complex. Examples of reducing agents useful in the practice of this invention include stannous salts such as stannous chloride, sodium dithionite, and ferrous salts such as ferrous sulfate.

In another embodiment of the present invention, radiopharmaceutical kits preferably comprising, bisamide-bisthiol compounds capable of complexing with technetium typically forming five coordinate oxotechnetium complexes ar thiol protected with a hydrophilic thiol protecting group such as the acetamidomethyl group and provided with a reducing agent in lyophilized form in a sterilized container or vial. In this form, the lyopholized composition can be readily reconstituted by adding only water having a pH in the range of 5 to 8 preferably physiological pH, or pertechnetate solution, thereby avoiding the use of alcoholic solutions required if other conventional thiol protecting groups are used. The bisamide, bisthiol compounds include N,N'-ethylene-bis(S-(protected)-2-mercaptoacetamide), N,N'-bis(S(protected)-2-mercaptoethyl) oxamide, and S-(protected)-2-mercaptoacetyl-glycyl(S-(protected)-cysteamine and derivatives substituted with groups such as those illustrated in structural formulae I, II, A, B, C, D, etc.

In certain cases, substituted derivatives of the bisamide-bisthiol compounds of this invention as illustrated in the above formulae can give a pair of diasteriomers when complexed with technetium. That is, the addition of a substitutent at a tetrahedral carbon atom will give rise to both syn- and anti-isomers. These isomers are referred to herein as peak (or compound) A and peak (or compound) B when separated by HPLC (high pressure liquid chromatography).

In general, the radiopharmaceutical preparation kit comprises a sterilized unit (or multidose) vial containing the purified compound and a reducing agent for technetium, preferably lyophilized. Each dose should consist of a sufficient amount of compound and reducing agent to complex with the required dose, normally less than about 0.5 mCi of $^{99m}$Tc per kg of body weight of the mammal to be tested. In use, the technetium, preferably as $^{99m}$Tc-pertechnetate in saline is injected asceptically into the vial and the mixture heated for a sufficient time to form the labelled complex. After cooling, the resulting radiopharmaceutical preparation is ready for use.

To test for renal function, a radiopharmaceutical preparation in accord with this invention having a suitable dose of radioactivity for the particular mammal is contained in a suitable pharmacological carrier such as normal saline. The radiopharmaceutical preparation is injected intravenously into the mammal. The kidney is then imaged by positioning the mammal under a scintillation camera in such a way that the kidney is covered by the field of view. The position of the liver will typically not interfere with the quality of the pictures taken of the right renal area because the complexes of the present invention are not significantly secreted by the biliary system.

In order to obtain high quality images the radiochemical yield of technetium complex should preferably be greater than 70% after reconstituting the lyophilized mixture and labelling. Lower yields will result in poorer image quality and undesirable purification steps would be required to produce high quality images.

The invention and its advantages will be further illustrated by the Examples that follow. Unless otherwise noted all percentages are weight percentage and all temperatures are in °C. In addition, the following abbreviations will have the meanings provided in the tabulation below:

Me—methyl
Et—ethyl
i$_{Pr}$—isopropyl
Bu—n-butyl
Ph—phenyl
Ac—acetyl
Tr—triphenylmethyl
Dpm—diphenylmethyl
Dcha—dicyclohexylamine
Su—succinimido
Acm—acetamidomethyl
DCC—dicyclohexylcarbodiimide
DCU—dicyclohexylurea
DME—dimethoxyethane
DMF—dimethylformamide
DMSO—dimethylsulfoxide
TLC—thin layer chromatography
MPLC—medium pressure liquid chromatography
BOC—t-butoxycarbonyl

EXAMPLE 1

Synthesis of N-(2-Benzoylthioethyl)-(2-benzoylthioacetyl) glycinamide (XII)

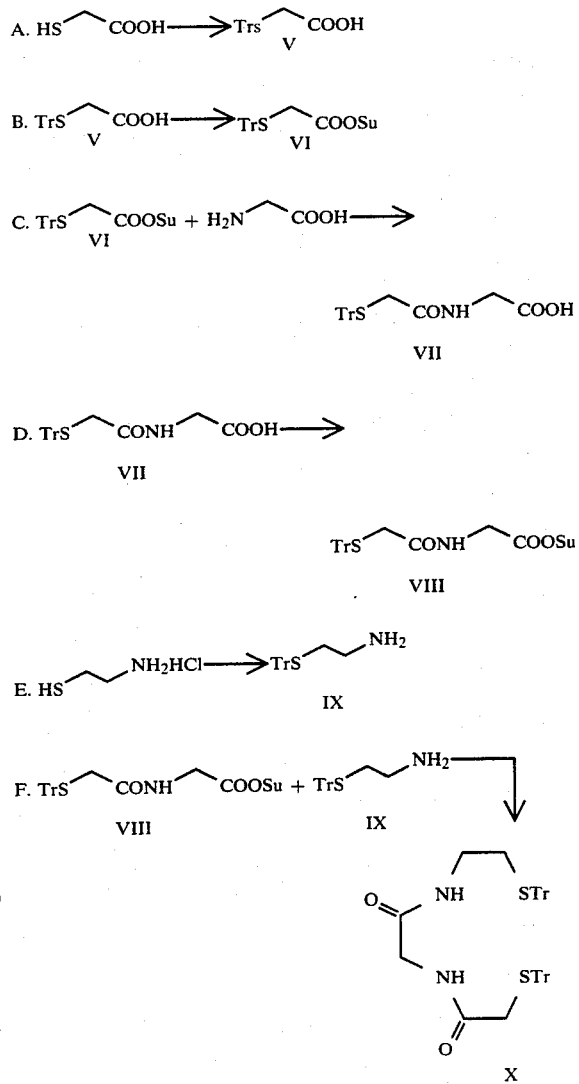

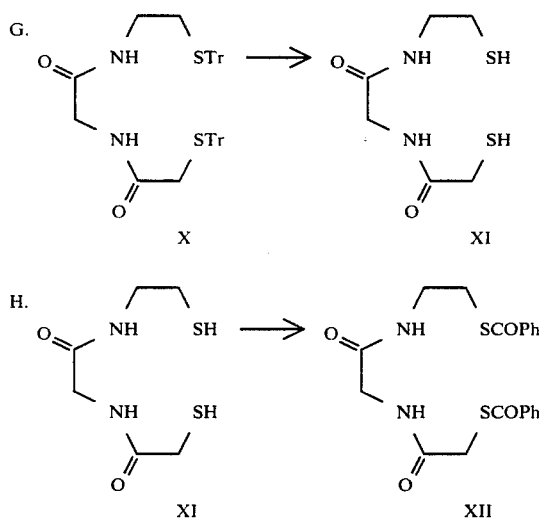

A. 2-(Triphenylmethylthio)acetic acid (V)

A mixture of distilled mercaptoacetic acid (20.87 g, 0.23 mmol), triphenylmethanol (60.0 g, 0.23 mol) and glacial acetic acid (200 ml) was heated to 70° C. Boron trifluoride etherate (32 ml, 0.25 mol) was added and the resulting brown mixture was stirred for 45 minutes at room temperature. The reaction mixture was then poured into water (500 ml), depositing a buff, granular solid which was filtered off, washed well with water then ether, and dried to give compound (V) (49.67 g, 67%). A further crop (12.27 g, 16%) was recovered from the ether washings, purified by recrystallization from benzene/hexanes. Both crops were homogeneous by TLC, mp 158.5°–160°.

B. Succinimido-(2-triphenylmethylthio)acetate (VI)

To a cooled solution of compound (V) (33.4 g, 0.10 mol) and N-hydroxysuccinimide (11.5 g, 0.10 mol) in DME (250 ml) was added a solution of DCC (22.7 g, 0.11 mol) in DME (50 ml) such that the temperature remained below 0° C. The resulting mixture was stored at 5° C. overnight and then filtered. The residue was washed well with $CH_2Cl_2$ and the combined filtrate and washings were concentrated in vacuo giving compound (VI) as a white precipitate that was filtered off, washed with ether and dried. The filtrate and ether washings gave a further crop, combined yield 36.53 g (85%), homogeneous by TLC. Recrystallization from ethyl acetate/hexanes gave an analytically pure sample, mp 178.5°–179°.

C. 2-Triphenylmethylthio)acetyl-glycine (VII)

To a solution of compound (VI) (30.0 g, 70 mmol) in DME (300 ml) and DMF (150 ml) was added a solution of glycine (5.25 g, 70 mmol) and $NaHCO_3$ (11.76 g, 140 mmol) in water (150 ml). The resulting solution was stirred at room temperature for 45 minutes then concentrated in vacuo to remove the DME. Dilution with water (300 ml) and treatment with 50% aqueous citric acid (60 ml) gave compound (VII) as a white solid which was recrystallized from ethyl acetate (yield 24.07 g, 88%), mp 160.5°–162.5°.

D. 2-(Triphenylmethylthio)acetyl-glycine, N-hydroxysuccinimide ester (VIII)

To a solution of compound (VII) (9.48 g, 24 mmol) and N-hydroxysuccinimide (2.79 g, 24 mmol) in DME (200 ml), cooled to −5° C., was added DCC (5.69 g, 28 mmmol) in DME (20 ml), such that the temperature remained below 0° C., and the resulting mixture was stored at 5° C. overnight. The precipitate was filtered off, washed well with $CH_2Cl_2$ and the filtrate and washings were evaporated to a pale yellow solid. Recrystallization of the latter from ethyl acetate gave (VIII) (10.48 g, 89%), mp 179°–182°.

E. 2-(Triphenylmethylthio)ethylamine (IX)

A mixture of 2-mercaptoethylamine hydrochloride (11.45 g, 0.10 mol) and triphenylmethanol (26.23 g, 0.10 mol) in trifluoracetic acid (100 ml) was stirred at room temperature for 30 minutes, then evaporated to a brown oil. Trituration of the oil with ether (500 ml) (complete color discharge) gave the trifluoroacetate salt of compound (IX) as a white precipitate which was filtered off and washed with ether. The washings were cooled to give a second crop, combined yield 30.8 g (70%). The trifluoroacetate salt of compound (IX) (14.0 g, 32 mmol) was partitioned between 1M aqueous NaOH and ether. Evaporation of the ether phase and recrystallization (ether/hexanes) gav compound (IX) (9.07 g, 88%), mp 93°–94°.

F. N-[2-(triphenylmethylthio)ethyl]-[2-(triphenylmethylthio) acetyl]-glycinamide (X)

A solution of ester (VIII) 2.45 g, 5.0 mmol) and amine (IX) (1.61 g, 5.0 mmol) in $CH_2Cl_2$ (70 ml) was stirred at room temperature for 3 hours, then stored at −5° C. overnight. The precipitated (X) was filtered off, washed well with cold $CH_2Cl_2$ and dried (yield 2.50 g, 72%). From the filtrate (washed with 5% aqueous $NaHCO_3$, dried ($MgSO_4$), evaporated and recrystallized from $CH_2Cl_2$, a further crop was obtained, combined yield 3.11 g (90%), mp 191°–193°.

G. N-(2-Mercaptoethyl)-(2-mercaptoacetyl)glycinamide (XI)

To a solution of the bis-triphenylmethyl derivative compound (X) (5.40 g, 7.8 mmol) in trifluoroacetic acid (30 ml) cooled in an ice bath, was added triethylsilane (2.6 ml, 16.3 mmol). Immediate color discharge and formation of a white precipitate was observed. The mixture was diluted with hexanes (40 ml) and water (40 ml) the aqueous phase was separated, washed with several portions of hexane, filtered through celite and evaporated to a colorless oil. Trituration of the oil with isopropanol gave compound (XI) as a white solid which was recrystallized from isopropanol (yield 1.50 g, 92%). A further recrystallization from $CHCl_3$ gave an analytically pure sample, mp 128°–130°.

H. N-(2-Benzoylthioethyl)-(2-benzoylthioacetyl) glycinamide (XII)

To a suspension of bisthiol compound (XI) (1.17 g, 5.6 mmol) in $CH_2Cl_2$ (50 ml) containing $^iPr_2NEt$ (2.0 ml, 11.5 mmol), cooled to 0° C., was slowly added PhCOCl (1.32 ml, 11.4 mmol) such that the temperature remained below 5° C. The resulting clear solution was stirred for 10 minutes, diluted with $CH_2Cl_2$ and acidified with 1M aqueous $H_2SO_4$ (30 ml, 30 mmol). The organic phase was separated, washed with 1M aqueous $H_2SO_4$, water and saturated brine, dried ($MgSO_4$) and evaporated to give a white solid. The solid was washed with ether and recrystallized from EtOH then $CH_2Cl_2$ to give compound (XII) (1.75 g, 75%), mp 146°–148°.

EXAMPLE 2

Synthesis of (2-Benzoylthioacetyl)-glycyl-(S-benzoyl)cysteine methyl ester (XVI)

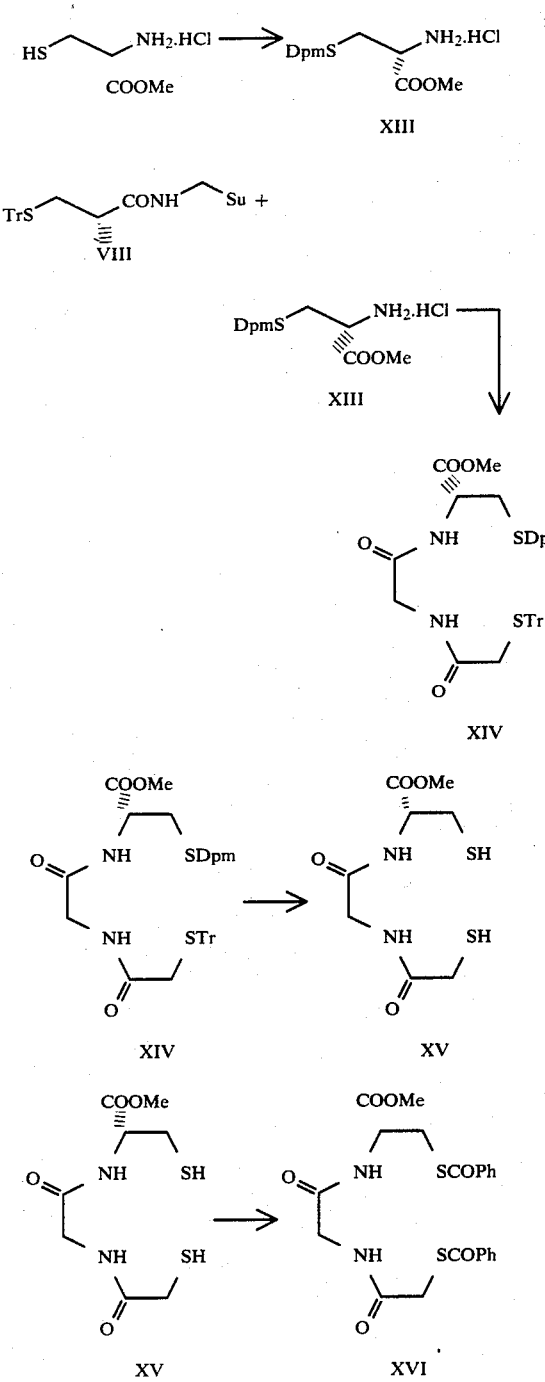

A. (S-Diphenylmethyl)cysteine methyl ester hydrochloride (XIII)

A solution, of cysteine methyl ester hydrochloride (see Zervas and Theodoropoulos, *J. Am. Chem. Soc.* 78:1359, (1956) (17.14 g, 0.10 mol) and diphenylmethanol (18.4 g, 0.10 mol) in $CF_3COOH$ (100 ml) was stirred at room temperature for 15 minutes then evaporated to an orange oil. The oil was taken up in ether, washed with 5% aqueous $NaHCO_3$ until all acid had been removed, dried ($Na_2SO_4$) and filtered to give a clear colorless solution. HCl gas was passed through the solution precipitating compound (XIII) as a white solid which was recrystallized ($^i$PrOH/$CH_3OH$), yield 26.57 g (79%), mp 161°–3°.

B. (2-Triphenylmethylthioacetyl)-glycyl-(S-diphenylmethyl)-cysteine methyl este (XIV)

A solution of 2-(triphenylmethylthio)acetyl-glycine, N-hydroxy succinimide ester (VIII) (4.88 g, 10 mmol) and compound (XIII) (3.38 g, 10 mmol) in $CH_2Cl_2$ (150 ml) containing $^iPr_2NEt$ (1.75 ml, 10.1 mmol) was stirred at room temperature for 3 hours, then washed with 1M aqueous $KHSO_4$, dried ($MgSO_4$) and evaporated to a foam. Chromatography (MPLC, 1–5% $CH_3OH/CH_2Cl_2$) and crystallization (EtOAc/hexane) gave compound (XIV) (5.51 g, 82%), mp 123°–5°.

C. Mercaptoacetyl-glycyl-cysteine methyl ester (XV)

A solution of compound (XIV) (5.04 g, 7.5 mmol) in $CF_3COOH$ (30 ml) was treated with triethylsilane (3.0 ml, 18.8 mmol). The resulting slightly colored suspension was stirred at room temperature overnight, then partitioned between water and hexane. From the aqueous phase was obtained an oil which was chromatographed (MPLC, 2–10% $CH_3OH/CH_2CL_2$) and triturated with ether to give compound (XV) (1.44 g, 72%). Recrystallization from $CH_2Cl_2$/ether gave an analytically pure sample, mp 67°–9°.

D. (2-Benzoylthioacetyl)-glycyl-(S-benzoyl)-cysteine methyl ester (XVI)

To a solution of compound (XV) (1.04 g, 3.9 mmol) in $CH_2Cl_2$ (40 ml) containing $^iPr_2NEt$ (1.4 ml, 8 mmol) cooled to 0° C., was slowly added PhCOCl (0.91 ml, 7.8 mmol). The resulting solution was stirred for 30 minutes, washed with 1M aqueous $H_2SO_4$, water and saturated brine and evaporated to an oil. Trituration of the oil with ether gave compound (XVI) (1.68 g, 91%). Recrystallization twice from EtOH gave an analytically pure sample (0.93 g, 50%), mp 138–140°.

EXAMPLE 3

Synthesis of (2-Acetamidomethylthio)acetyl-glycyl-(S-acetamidomethyl) cysteine methyl ester (XVII)

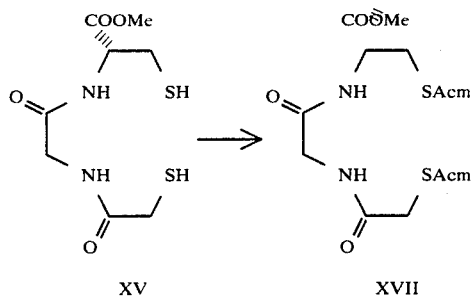

A solution of thiol compound (XV) (280 mg, 1.05 mmol) and acetamidomethanol (187 mg, 2.1 mmol) in CF$_3$COOH (4 ml) was stirred at room temperature for 90 minutes, then poured into ether (50 ml) causing the product to precipitate. The precipitate was filtered off, washed with ether and dried in vacuo, yield 239 mg, 54%.

EXAMPLE 4

Synthesis of (2-Acetamiodomethylthioacetyl)-glycyl-(S-acetamidomethyl)cysteine (XIX)

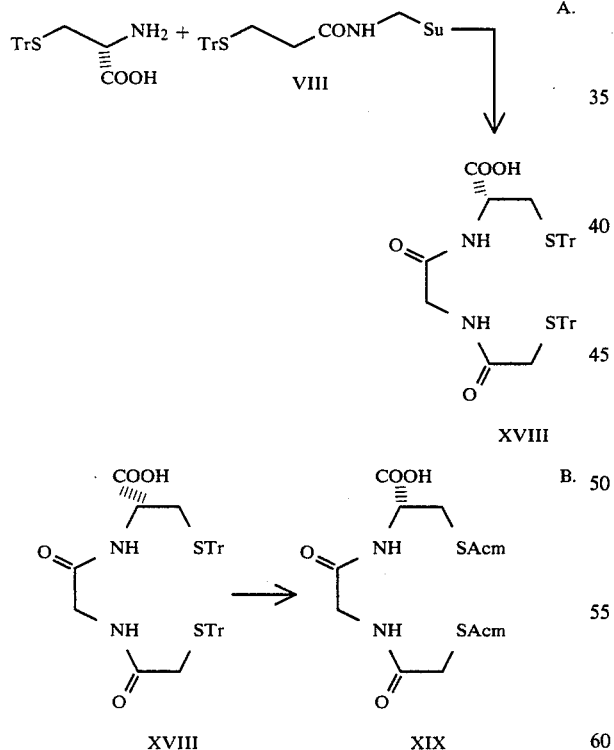

A.
(2-Triphenylmethylthioacetyl)-glycyl-(S-triphenylmethyl) cysteine (XVIII)

A solution of compound (VIII) (4.88 g, 10 mmol) was dissolved in a mixture of DME (50 ml) and DMF (20 ml) and cooled to 0° C., and treated with a solution of S-(triphenylmethyl)cysteine (See Hiskey and Adams, *J. Org. Chem.* 3: 1340, (1965)) (3.63 g, 10 mmol) in DME (25 ml) and 1M aqueous NaOH (10 ml, 10 mmol) containing NaHCO$_3$ (0.84 g, 10 mmol). The resulting solution was allowed to warm to room temperature after stirring for 50 minutes, 1M aqueous KHSO$_4$ (30 ml) was added and a white gummy solid precipitated. The resulting mixture (pH 4) was extracted with CH$_2$Cl$_2$ (3×50 ml). The CH$_2$Cl$_2$ was washed with water, then saturated brine, dried (MgSO$_4$), filtered and evaporated to give compound (XVIII) as an oil. Recrystallization from MeOH gave compound (XVIII) as a white solid (7.24 g, 98%). Recrystallization of the material from MeOH gave an analytically pure sample homogeneous by TLC, mp 129°–135°.

B.
(2-Acetamidomethylthioacetyl)-glycyl-(S-acetamidomethyl) cysteine (XIX)

A solution of acetamidomethanol in CF$_3$CO$_2$H (1.3 ml, 1.6M, 2.08 mmol) was added to a solution of compound (XVIII) (0.748 g, 1.01 mmol) in CF$_3$CO$_2$H (5 ml) and the resulting brown solution stirred for 3 hours. The addition of ether (45 ml) caused the color to discharge and a white precipitate formed. This was Schlenk-line filtered and washed with ether. The crude solid, compound (XIX), (0.245 g, 62%) was very hygroscopic it was homogeneous by TLC and could be recrystallized with loss from isobutanol.

EXAMPLE 5

Synthesis of (2-Benzoylthioacetyl)-glycyl-(S-benzoyl) cysteinyl-glycine methyl ester (XXV)

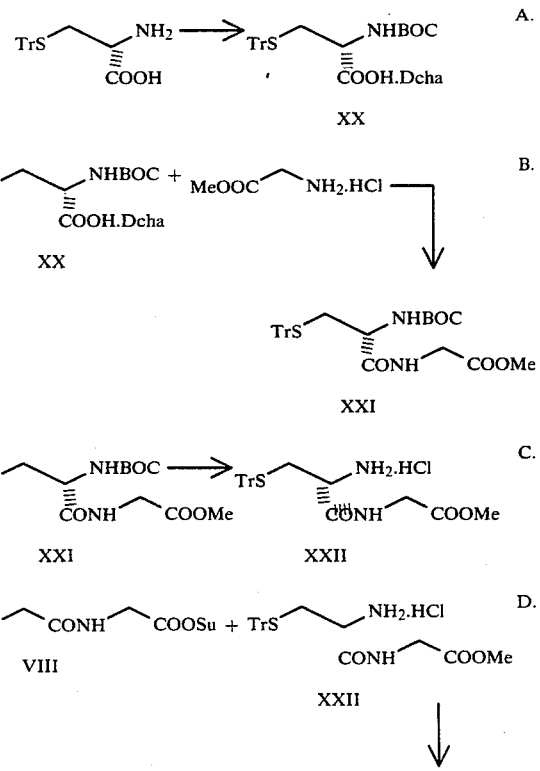

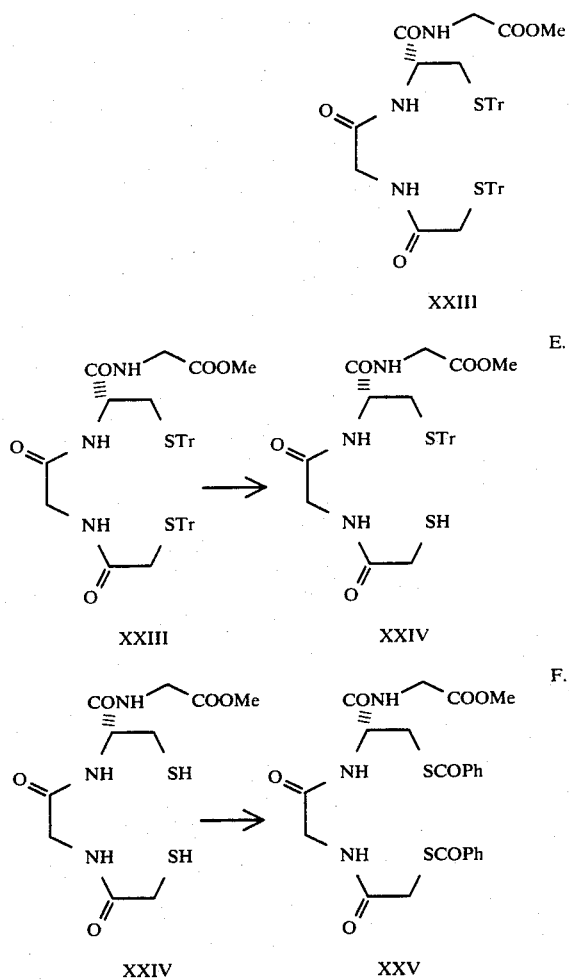

A. N-boc-S-trityl-cysteine, dicyclohexylammonium salt (XX)

To a solution of S-trityl cysteine (see Hiskey and Adams, *J. Org. Chem.*, 30:1340, (1965)) (36.3 g, 0.10 mol) in dioxane (200 ml) and 1M aqueous NaOH (100 ml, 0.10 mol) was added di-t-butyl carbonate (25.36 g, 0.12 mol). The resulting opaque solution became warm and effervesced and the pH fell from 12 to 8 over one hour. After stirring for 90 min, 50% aqueous citric acid (40 ml) was added and the resulting mixture (pH 4) was extracted with ether. The ether was washed with water, then saturated brine, dried (MgSO4), filtered and evaporated to give N-BOC-S-(triphenylmethyl)-cysteine as an oil. Half of this material was dissolved in ether (200 ml) and treated with dicyclohexylamine (10 ml, 50 mmol) to give compound (XX) as a white precipitate which was filtered off, washed with ether and dried (25.1 g, 78%), mp 205°–207°.

B. N BOC-S-(triphenylmethyl)-cysteinyl-glycine methyl ester (XXI)

A solution of compound (XX) (19.33 g, 30.0 mmol), glycine methyl ester hydrochloride (see Curtis and Goebel, *J. Prakt. Chem.*, 37:150, (1888)) (3.47 g, 30.0 mmol) and N-hydroxysuccinimide (3.46 g, 30.1 mmol) was cooled to 0° C., then treated with a solution of DCC (6.87 g, 33.4 mmol) in CH2Cl2 (20 ml). The mixture was stirred, cold, for 30 minutes, then at room temperature for 3 hours. The precipitate was filtered off, washed with CH2Cl2, and the combined filtrate and washings were washed with 1M aqueous KHS04, 5% aqueous NaHCO3 and saturated brine, dried (MgSO4) and evaporated. Recrystallization of the resulting solid gave compound (XXI) (12.3 g, 77%), mp 167°–9°.

C. S-(Triphenylmethyl)-cysteinyl-glycine methyl ester hydrochloride (XXII)

To a mixture of compound (XXI) (2.39 g, 4.5 mmol) and anhydrous CH3COOH (40 ml) was added boron trifluoride etherate (2 ml, 16 mmol). The resulting yellow solution was stirred for 35 minutes then poured into ice-cold 2M aqueous NH4OH (400 ml), precipitating a white gum. The gum was extracted into CH2Cl2, the solution was evaporated, and the residue was redissolved in ether. Passage of HCl through the ether solution gave compound (XXII) as a hygroscopic white powder (1.86 g, 88%).

D. (2-Triphenylmethylthioacetyl)-glycyl-(S-triphenylmethyl) cysteinyl-glycine methyl ester (XXXIII)

A solution of compound (VIII) (1.69 g, 3.45 mmol) and compound (XXII) (1.63 g, 3.45 mmol) in CH2Cl2 (50 ml) containing iPr2NEt (0.62 ml, 3.55 mmol) was stirred at room temperature for 60 min during which time product started to precipitate. Precipitation was completed by refrigeration to give compound (XXIII) as a white solid (3.52 g, 91%), mp 195°–7°.

E. Mercaptoacetyl-glycyl-cysteinyl-glycine methyl ester (XXIV)

A solution of compound (XXIII) (2.02 g, 2.5 mmol) in CF3COOH (10 ml) was treated with triethylsilane (0.84 ml, 5.3 mmol), resulting in immediate color discharge and formation of a white precipitate. The mixture was partitioned between hexane and water, followed by evaporation of the aqueous phase to give a colorless oil. Crystallization of the oil (iPrOH/CH3OH) gave compound (XXIV) (0.66 9, 82%), mp 149°–151°.

F. (2-Benzoylthioacetyl)-glycyl-(S-benzoyl)cysteinyl-glycine methyl ester (XXV)

To a suspension of compound (XXIV) (0.59 g, 1.8 mmol) in CH2Cl2 (18 ml) containing iPr2NEt (0.65 ml, 3.7 mmol), cooled to 0° C., was slowly added benzoyl chloride (0.43 ml, 3.7 mmol). The resulting clear solution was stirred for 30 minutes, diluted with ethyl acetate, washed with 0.5M aqueous H2SO4 and water, dried (MgSO4) and evaporated to give 0.91 g (94%) of crude compound (XXV). Chromatography (MPLC, 2–10% CH3OH/CH2Cl2) and recrystallization (CH3OH) gave pure compound (XXV) (0.66 g, 68%), mp 181°–3°.

EXAMPLE 6

Synthesis of N-[-2-(benzoylthio)ethyl]-N'-[1-carbomethoxy-(2-benzoylthio)ethyl]oxamide (XXXI)

A.

XXVI

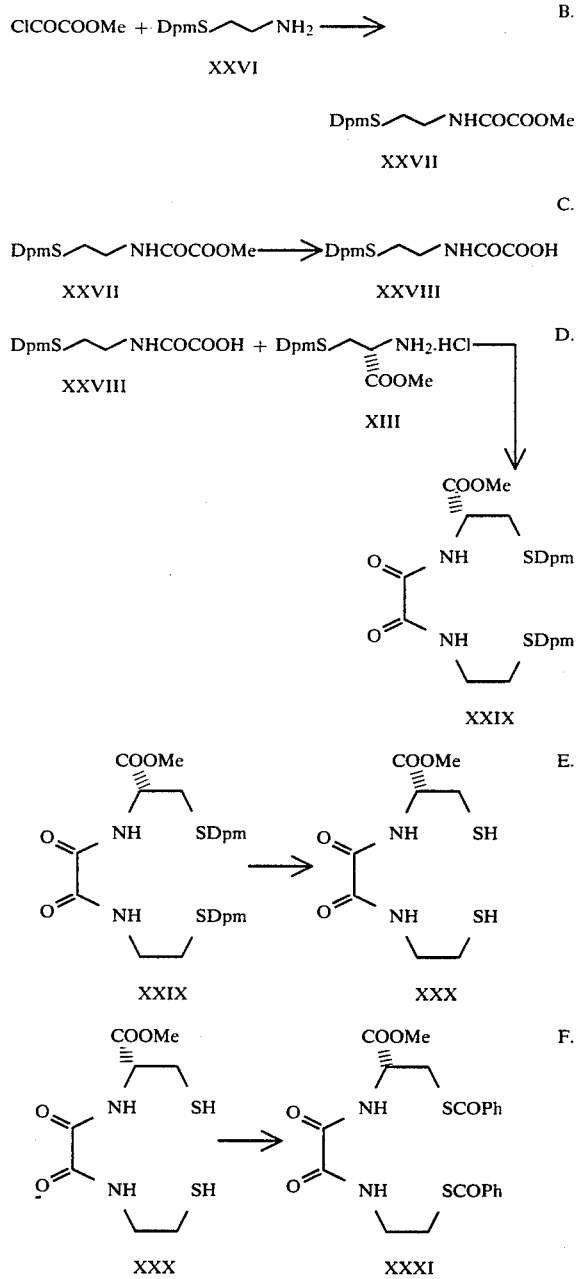

B. N-[2-(diphenylmethylthio)ethyl]oxamic acid methyl ester (XXVII)

To a stirred solution of compound (XXVI) (13.298 g, 0.0546 mol) and diisopropylethylamine (9.50 ml, 0.0546 mol) in $CH_2Cl_2$ (70 ml) at 0° under Ar, was added dropwise, methyloxayl chloride (5.10 ml, 0.0546 mol) in $CH_2Cl_2$ (8 ml), such that the temperature was at or below 0°. This mixture was stirred for 30 minutes at 0° and then allowed to warm to room temperature over 2 hours. The solution was washed with 1N HCl (40 ml), water (40 ml), saturated aqueous NaCl (40 ml), dried ($MgSO_4$) and the solvent removed in vacuo. The crude white solid thus obtained was homogeneous by TLC. Recrystallization from ethanol yielded 15.476 g (86%), mp 88°–89°.

C. N-[2-(diphenylmethylthio)ethyl-9 oxamic acid (XXVIII)

A solution of compound (XXVII) (13.562 g, 0.041 mol) in benzene (270 ml), ethanol (135 ml) and 2N NaOH (100 ml) was stirred for 20 minutes at room temperatue. 2N HCl (100 ml) was added and most of the solvent removed in vacuo. $CH_2Cl_2$ (200 ml) was added, the aqueous layer separated and extracted with $CH_2Cl_2$ (2×100 ml). The $CH_2Cl_2$ solutions were combined and washed with water (2×100 ml), saturated aqueous NaCl, dried ($MgSO_4$) and the solvent removed in vacuo. The crude product was dried in vacuo, 11.530 g (89%) collected, mp 100°–101.5°. Recrystallization of a small amount from benzene resulted in no change in the mp.

D. N-[2-(diphenylmethylthio)ethyl]-N'-[1-carbomethoxy-2-(diphenylmethylthio) ethyl]-oxamide (XXIX)

To a cooled solution of amine compound (XIII) (10.721 g, 31.7 mmol), acid compound (XXVIII) (10.008 g, 31.7 mmol) diisopropylethylamine (5.6 ml, 32.1 mmol), and N-hydroxysuccinamide (3.648 g, 31.7 mmol) in DME (250 ml) was added DCC (7.259 g, 35.2 mmol) in $CH_2Cl_2$ (25 ml). After 2 hours the cooling bath was removed and the reaction was allowed to stir at room temperature overnight. The DCU was filtered off and washed with $CH_2Cl_2$ (100 ml). The combined filtrate and washings were combined and taken to dryness in vacuo. The crude material was redissolved in $CH_2Cl_2$ and washed with 1N $KHSO_4$ (50 ml), $H_2O$ (4×50 ml), 5% aqueous $NaHCO_3$ (50 ml) saturated aqueous NaCl (50 ml), dried ($MgSO_4$), and the solvent removed in vacuo. Recrystallization (EtOAc/hexanes) gave compound (XXIX), yield 16.425 g (87%), mp 131°×132°.

E. N-[2-mercaptoethyl]-N'-[1-carbomethoxy-2-mercaptoethyl]oxamide (XXX)

A solution of compound (XXIX) (3.039 g, 5.0 mmol) in $CF_3CO_2H$ (30 ml), treated with triethylsilane (1.7 ml, 10.7 mmol), was allowed to stir overnight, under Ar, at room temperature. The reaction was quenched with water (30 ml) and then extracted with hexane (3×50 ml). From the aqueous phase a slightly yellow viscous oil was obtained, yield. 1.060 g, 80%. This oil was dissolved in MeOH (15 ml), $^i$-PrOH (60 ml) was added and then most of the MeOH removed in vaco. Cooling gave 713 mg, 67%, of compound (XXX), mp 111.5°–112.5°. Recrystallization of this material from $^i$PrOH/$CH_3OH$,

A. 2-(Diphenylmethylthio)ethylamine (XXVI)

A mixture of 2-mercaptoethylamine hydrochloride (12.058 g, 0.106 mol) and diphenylmethanol (20.062 g, 0.109 mol) in $CF_3CO_2H$ (180 ml) was stirred at room temperature for 5.5 hours, then evaporated to a brownish/orange oil. Ether (500 ml) and 2N NaOH (200 ml) were added. The ether layer was washed with water (3×100 ml), saturated aqueous NaCl (100 ml), dried ($MgSO_4$) and most of the ether removed in vacuo. The solution was cooled to −10° giving white crystalline compound (XXVI). This material was filtered, washed with cold ether and dried in vacuo (18.323 g, 71%). The volume of the combined washing and filtrate was reduced and cooled (−10° C.) giving a second crop, combined yield 20.479 g (84%), mp 74°.

as above, gave analytically pure material, mp. 118°–119°.

F. N-[2 (benzoylthio)ethyl]-N'-[1-carbomethoxy-(2-benzoylthio) ethyl]oxamide (XXXI)

To a cooled solution of compound (XXX) (1.013 g, 3.8 mmol) and diisopropylethylamine (1.35 ml, 7.8 mmol) in $CH_2Cl_2$ (50 ml) was added, over 10 minutes, benzoyl chloride (0.9 ml, 7.8 mmol). The reaction was allowed to warm to room temperature, with stirring, over 2 hours. The solution was washed with 1M $H_2SO_4$ (25 ml), $H_2O$ (25 ml), saturated aqueous NaCl (25 ml), dried ($MgSO_4$), and most of the solvent removed in vacuo. Ether (100 ml) was added to precipitate the product, which was collected, washed with ether and air dried, yield 1.39 g (77%). An additional crop was obtained from the combined filtrate and washings (total yield, 1.47 g, 82%). Chromatography (MPLC, 1% $CH_3OH/CH_2Cl_2$) gave analytically pure material, yield 1.17 g (80%), mp 159.5°–161°.

EXAMPLE 7

Synthesis of N, N'-bis(2-mercaptoethyl)oxamide (XXXII)

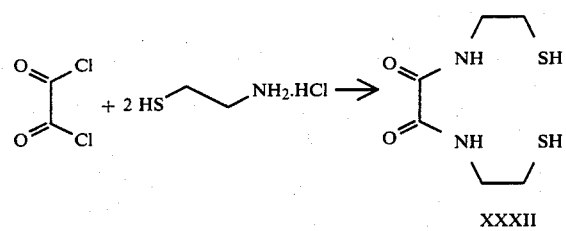

To a stirred suspension of 2-mercaptoethylamine hydrochloride (4.43 g, 40 mmol) in freshly distilled $CH_3CN$ (60 ml), cooled to −5° under Ar, was added diisopropylethylamine (16.0 ml, 92 mmol). After 5 minutes, chlorotrimethylsilane (6.6 ml, 52 mmol) was added in one portion, causing the complete solution of all suspended material. After 10 minutes, a solution of oxalyl chloride (1.76 ml, 20 mmol) in $CH_3CN$ (10 ml) was added dropwise, such that the temperature remaiained below 0°, followed by diisopropylethylamine (7.0 ml, 40 mmol) again such that the temperature remained below 0°. The resulting solution was stirred for 30 minutes at or below 0°, then warmed to room temperature during 2 hours. The solution was then poured into ice/water (150 ml), immediately precipitating the crude product compound (XXXII) as white precipitate which was collected, washed well with water, and dried in vacuo (18 hours at room temperature followed by 12 hours at 67°): yield 3.5 g (87%). This material (soluble only in DMSO, trifluoroacetic acid and aqueous alkali) was normally used without purification. Analytically pure material was obtained as follows.

With rigorous exclusion of oxygen, an Ar-purged solution of sodium hydroxide (39.4 g, 1.0 mmol) in doubly distilled deionized water (50 ml) was added to the crude dithiol (1.076 g, 0.49 mmol). The mixture was stirred for 30 minutes followed by removal of a small amount of undissolved material by anaerobic filtration. To the filtrate was added 12M aqueous HCl (2.0 ml, 24 mmol) giving an immediate white precipitate, which was collected, washed with distilled, deionized water (50 ml) and dried in vacuo at 67°, yield 500 mg of pure compound (XXXII) mp 167°.

EXAMPLE 8

N,N'-bis(2-carbomethoxy-2-benzoylthioethyl)oxamide (XXXIV)

A. N,N'-bis(2-carbomethoxy-2-mercaptoethyl)oxamide (XXXIII)

Compound (XXXIII) was prepared in a manner similar to N-N'-bis-(2mercaptoethyl)oxamide compound (XXXII), using cysteine methyl ester hydrochloride in place of 2- mercaptoethylamine hydrochloride. Yield 2.9 g (56%). Chromatography (MPLC 1% $MeOH/CH_2Cl_2$) gave analytically pure material, mp. 150.5°–151°.

B. N,N'-bis(1-carbomethoxy-2-benzoylthioethyl) oxamide (XXXIV)

A solution of compound (XXXIII) (2.140 g, 6.6 mmol) and diisopropylethylamine (2.3 ml, 13.2 mmol) in $CH_2Cl_2$ (50 ml) was cooled to 0°. Benzoyl chloride (1.5 ml, 13.2 mmol) was added in one portion. The reaction was stirred at 0° for 30 minutes and then allowed to warm to room temperature. This solution was washed with 1M $KHSO_4$ (50 ml), $H_2O$ (50 ml), saturated aqueous NaCl (50 ml), dried ($MgSO_4$), and the solvent removed in vacuo. The slightly off-white solid was recrystallized from CHClphd 3/hexanes, yield 2.518 g (72%), mp. 185°–186°.

EXAMPLE 9

Synthesis of the (Tc-99) oxo-bis(1,2-ethanediolato) technetate(+5) ion (XXXV)

$Bu_4N^+TcOCl_4^-$ + HO⌒OH ⟶

-continued

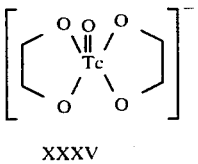

XXXV

Solutions of this complex were prepared by the following modification to the procedure of DePamphilis (B.V. DePamphilis, Ph.D Thesis, M.I.T. 1980).

To a pale green solution of Bu₄NTcOCl₄ (B.V. DePamphilis, Ph.D. Thesis, M.I.T. 1980) (107 mg, 0.21 mmol) in CH₃OH (2 ml) containing ethylene glycol (0.10 ml, 1.79 mmol) was slowly added a methanolic solution of sodium acetate (0.75M, 2 ml, 1.5 mmol). The color of the solution passed from green through dark blue to the clear, stable, deep purple characteristic of oxo-bis-diolato-technetium(+5) complexes. The resulting solution was thus approximately 0.05M in the oxo-bis(1,2-ethanediolato)technetate ion (XXXV).

EXAMPLE 10

Synthesis of (Tc-99) tetraphenylarsonium-oxo-[N-(1-carboxy-2-mercaptoethyl)-(mercaptoacetyl)-glycinimido]technetate(+5) (XXXVI)

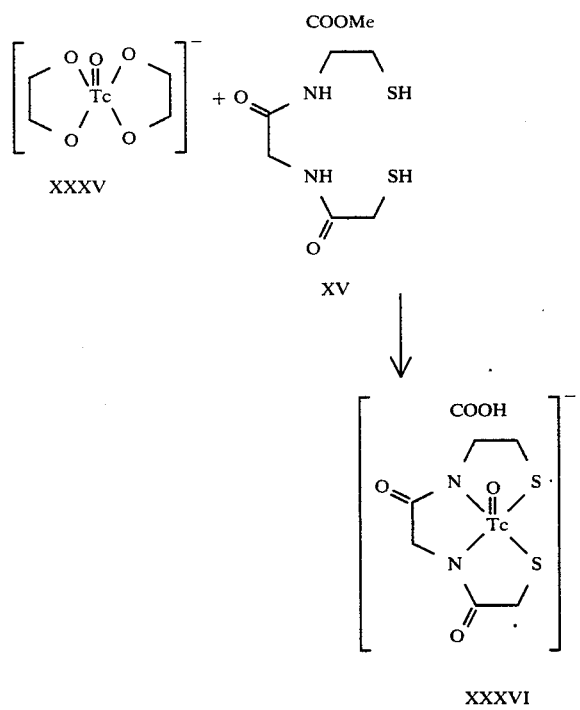

A solution of [TcO(OCH₂CH₂O)₂]⁻¹ (XXXV) was prepared by the reaction of Ph₄AsTcOCl₄ (132 mg, 0.21 mmol) in MeOH (2 ml) with ethylene glycol (0.10 ml, 1.79 mmol) followed by a methanolic solution of NaOAc (0.75M, 2 ml, 1.5 mmol). This purple solution was added to the ester compound (XV) (64 mg, 0.24 mmol) dissolved in 0.2M aqueous NaOH (12 ml, 2.4 mmol), causing discharge of the purple color to give a deep red solution. This solution was acidified by the dropwise addition of 2M aqueous HCl (2 ml, 4 mmol) causing the product (mixed syn and anti isomers) to separate as a fine yellow precipitate. An aqueous solution of Ph₄AsCl.H₂O (200 mg) was added to complete the precipitation and the product was filtered off, washed with water and dried in vacuo to give compound (XXXVI) (127 mg, 81%), which was recrystallized from acetonitrile. The tetraphenylarsonium salt compound (XXXVI) could be metathesized to the sodium salt, HPLC analysis of which showed the presence of two peaks corresponding to the syn and anti isomers.

EXAMPLE 11

Synthesis of (Tc-99) tetraphenylarsonium oxo[N,N'-bis(2-mercaptoethyl)oximido]-technetate(+5) (XXXVII) Method 1

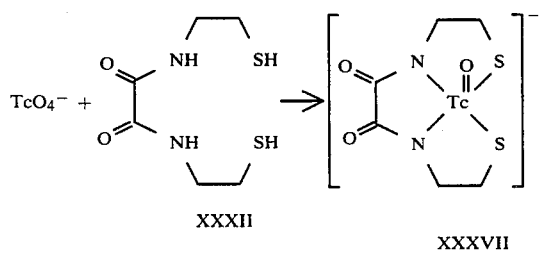

To a warm (60°) stirred solution of NH₄⁹⁹TcO₄ (0.52 ml of a 0.38M solution, 0.20 mmol) and bisthiol compound (XXXII) (164 mg, 0.8 mmol) in ethanol (50 ml) and 2M aqueous NaOH (50 ml) was slowly added a solution of sodium dithionite (100 mg, 0.60 mmol) in 2M aqueous NaOH (5 ml). During the addition, the reaction mixture turned yellow then brown, and, upon further heating, orange. After allowing the volume to reduce to approximately 40 ml the reaction mixture was allowed to cool to room temperature. The addition of a solution of tetrabutylammonium bromide (483 mg, 1.7 mmol) in water gave precipitate which was dried in vacuo to give 150 mg of impure product contaminated with pertechnetate (IR analysis). Since purification by recrystallization was unsuccessful, reverse-phase chromatography using a C₁₈ SEP-PAK ™ (Waters Associates) was employed.

A C₁₈ SEP-PAK ™ was equilibrated with methanol (10 ml) followed by 0.05M aqueous ammonium sulphate (10 ml). Crude product, dissolved in 15 ml of 25% acetone in water, was applied to an equilibrated C₁₈ SEP-PAK ™ in 0.5 to 1.5 ml portions. Elution with 0.05M aqueous ammonium sulphate (10 ml) completely removed the pertechnetate. Subsequent elution with methanol (5 ml) gave a yellow solution. The methanolic fractions were combined, evaporated, redissolved in acetone and water and treated with tetraphenylarsonium chloride hydrate (0.25 g, 57 mmol) to give compound (XXXVII) as an orange precipitate. The precipitate was collected, washed with water then ether and dried in vacuo, yield 30 mg (21%). Method 2

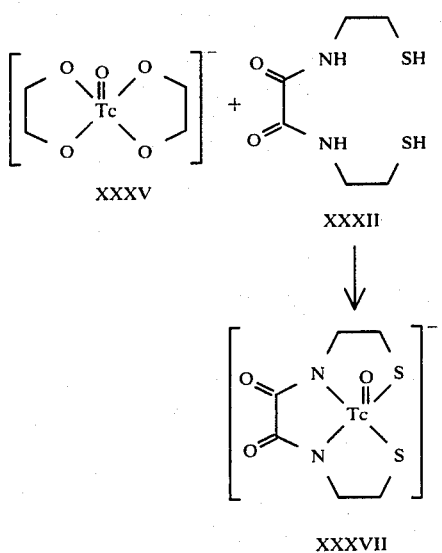

XXXV + XXXII

↓

XXXVII

A purple methanolic solution of compound (XXXV) (0.22 mmol in 10 ml, prepared as described above), Example 9, was added dropwise to a warm (50°–60°) colorless solution of bisthiol compound (XXXII) (166 mg, 0.8 mmol) in ethanol (75 ml) and 3M aqueous NaOH (75 ml). The resulting clear yellow solution was further heated to reduce the volume to 50 ml and then allowed to cool to room temperature. A solution of tetraphenylarsonium chloride hydrate (0.25 g, 057 mmol) in water (5 ml) was added and the resulting solution was allowed to stand overnight, depositing compound (XXXVII) as small orange needles which were collected, washed with water and dried in vacuo, yield 127 mg (82%). Recrystallization from CH$_2$Cl$_2$/hexane gave dark gold/orange blocks, mp. 227°–228°.

EXAMPLE 12

Synthesis of (Tc-99)tetraphenylarsonium-oxo-[N,N'-bis-(1-carboxy-2-mercaptoethyl)-oximido]-technetate(+5) (XXXVIII)

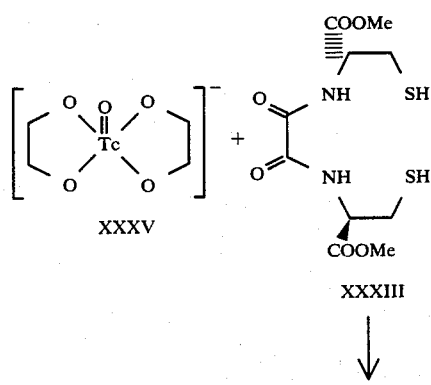

XXXV + XXXIII

↓

-continued

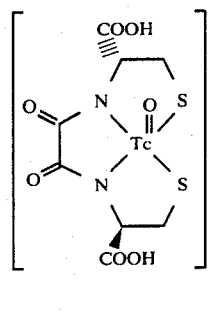

XXXVIII

A purple methanolic solution of compound (XXXV) (0.21 mmol in 10 ml, prepared as described above, Example 9) was added dropwise to a colorless solution of bis thiol compound (XXXIII) (97 mg, 0.30 mmol) in 2N NaOH (10 ml). The resulting clear yellow-orange solution was allowed to sit at room temperature until the volume was 10 ml. Tetraphenylarsonium chloride hydrate (0.25 g, 0.57 mmol) in water (5 ml) was added. This solution was filtered and the pH adjusted to 1–2, with concentrated HCl. A yellow-orange precipitate formed immediately. This was allowed to sit overnight. The solid was filtered and dried in vacuo, yield 149 mg (86%). This material was recrystallized from MeOH-/Et$_2$O, resulting in dark orange blocks. These blocks were dried overnight in vacuo at room temperature and then 48 hours at 78°, yield 100 mg, 67%, mp 195°–197°.

EXAMPLE 13

$^{99m}$Tc Complexation by Dithionite Reduction of a Basic Aqueous Ethanolic Solution of Ligand The ligand XI, XII, XV, XVI, XIX, XXIV, XXV, XXX, XXXI, XXXII, XXXIII or XXXIV (3.0 mg) was dissolved in EtOH (0.3 ml) by heating in a boiling water bath for one minute. A solution of NaOH (0.5M aqueous, 0.3 ml) was added and the mixture was heated in the boiling water bath for 5 minutes. Saline (0.3 ml) containing e.g. 3 mCi of $^{99m}$TcO$_4$− was added followed by 0.5 mg of Na$_2$S$_2$O$_4$ (sodium dithionite). The mixture was swirled for 30 seconds and the pH was adjusted to 7–8 with dropwise addition of approximately 0.3 ml of 0.5M aqueous HCl. The solution was allowed to stand for 20 minutes before use. The radiochemical yield was >90% of the combined isomers, in all cases.

EXAMPLE 14

$^{99m}$Tc Complexation By Stannous Ion Reduction of a Basic Aqueous Ethanolic Solution of the Lioand A stannous glucoheptonate kit (NEN-GLUCOSCAN TM) (containing 200 mg sodium glucoheptonate and 0.06–0.07 mg stannous chloride dihydrate) was reconstitued with 4 ml saline. A 30 ul aliquot of this solution was added to 0.3 ml of saline containing e.g. 3 mCi of $^{99m}$TcO$_4$− in a closed vial. To a second vial, containing 3.0 mg of ligand XI, XII, XV, XVI, XIX, XXIV, XXV, XXX, XXXI, XXXII, XXXIII or XXXIV dissolved, by heating, in 0.3 ml EtOH was added 0.3 ml of 0.5M aqueous NaOH and the mixture was heated in a boiling water bath for 5 minutes. The solution from the first vial was added to the solution in second vial. The vial was closed, shaken, then, heated in a boiling water bath for 5 minute. The pH was adjusted to 7-8 by dropwise addition of 0.3 ml of 0.5M aqueous HCl. The radiochemical yield was ca. 75% combined isomers.

EXAMPLE 15

$^{99m}$Tc Complexation By Stannous Ion Reduction at Neutral pH in an Isotonic Saline Solution of Ligand A stannous glucoheptonate kit (NEN-GLUCOSCAN TM) was reconstituted with 4 ml saline. A 30 microliter aliquot of this solution was added to a closed sterile vial containing 3 mg of ligand (XIX). To the vial was then added 1 ml of saline containing e.g. 3 mci $^{99m}$TcO$_4$− and the vial was shaken and heated in a boiling water bath for approximately 10 minutes. The radiochemical yield was 93.4% of the combined isomers. This formulation showed no free TcO$_4$− or hydrolyzed technetium TcO$_2$ by thin-layer chromatography.

EXAMPLE 16

$^{99m}$Tc Complexation by Modified Stannous Ion Reduction at Neutral pH in an Isotonic Saline Solution of Ligand A stannous glucoheptonate kit (NEN-GLUCOSCAN TM) to which had been added 1 mg SnCl$_2$·2H$_2$O, was reconstituted with 4 ml of sterile saline. A 30 ul aliquot of this solution was added to a sterile vial containing 3 mg of ligand (XIX) followed by the addition of approximately 1 ml of saline containing 5 to 15 mCi of $^{99m}$TcO$_4$−. The vial was then shaken and heated in a boiling water bath for approximately 10 minutes. The radiochemical yield (of the combined isomers) was 96.9%.

EXAMPLE 17

Comparison of the Renal Clearance of $^{99m}$Tc Complexes Formed with Comoounds XVI and XXXI Versus OIH in Normal Doos The diastereomeric $^{99m}$Tc complexes formed by reduction of pertechnetate in the presence of (2-benzoyl-thioacetyl)- glycyl-(S-benzoyl)-cysteine methyl ester (compound XVI) and N-2-(benzoylthio)ethyl)-N'-1-carbomethoxy-(2-benzoylthio)ethyl]oxamide (compound XXXI) were synthesized and separated by high pressure liquid chromatography. The two fractions collected from the products of synthesis in each case were denoted (XVIA), (XVIB), (XXXIA), and (XXXIB), respectively.

Samples of each fraction were mixed with appropriate amounts of $^{131}$I-OIH and coinjected into normal dogs placed under a gamma camera. Images were recorded at 1, 5, 10, 15, 20, 25, 30 and 35 minutes after administration. The initial image at one minute was used to collect 750,000 counts. All subsequent images were exposed for the same length of time as this first image, and the number of counts noted. Immediately after each count, a urine sample was drawn from the bladder via a indwelling catheter, and the $^{99m}$Tc ANd $^{131}$I activity determined using an ionization chamber. In this way, the counts collected in the camera images cound be related to absolute activity levels (mCi or $\mu$Ci). The animals were then observed until the urine samples were free of $^{99m}$Tc.

Table I below shows the data obtained in three animals for each of the four $^{99m}$Tc products tested. The values represent the calculated % total dose in the camera region of interest set over the bladder.

TABLE I

% Total Dose In Bladder Versus Time (gamma camera data)

| Compound No. | Time (min. post injection) | | | | | | |
|---|---|---|---|---|---|---|---|
| | 5 | 10 | 15 | 20 | 25 | 30 | 35 |
| (XVIA) | 13.13 | 38.08 | 49.99 | 57.29 | 63.73 | 63.67 | 66.64 |
| | 9.63 | 34.15 | 47.44 | 59.01 | 64.39 | 66.95 | 72.79 |
| | 3.25 | 33.73 | 46.89 | 56.40 | 62.63 | 58.77 | 63.08 |
| (XVIB) | 12.31 | 28.53 | 39.47 | 45.09 | 48.09 | 53.05 | 54.63 |
| | 10.03 | 33.78 | 45.88 | 53.55 | 60.94 | 64.60 | 73.12 |
| | 19.60 | 36.51 | 47.52 | 55.57 | 59.98 | 70.00 | 71.57 |
| (XXXIA) | 5.76 | 15.30 | 22.26 | 28.21 | 32.68 | 38.08 | 41.57 |
| | 4.12 | 12.39 | 15.99 | 21.59 | 25.47 | 30.43 | 31.19 |
| | 0.81 | 9.87 | 16.51 | 22.50 | 27.72 | 32.34 | 34.90 |
| (XXXIB) | 15.45 | 37.76 | 49.26 | 61.08 | 67.47 | 70.23 | 69.76 |
| | 12.59 | 28.47 | 41.85 | 48.71 | 55.87 | 60.72 | 61.09 |
| | 12.63 | 27.98 | 35.28 | 43.22 | 48.35 | 50.84 | 57.93 |

In Table II can be seen the average % total dose valus observed in the urine samples collected at each time point. Also quoted in parentheses are the standard deviation and standard error of the mean.

TABLE II

Average % Total Dose in Urine Samples

| Compound No. | Time (min. post injection) | | | | | | |
|---|---|---|---|---|---|---|---|
| | 5 X SD SEM | 10 X SD SEM | 15 X SD SEM | 20 X SD SEM | 25 X SD SEM | 30 X SD SEM | 35 X SD SEM |
| (XVIA) | 8.67 | 35.32 | 48.11 | 57.57 | 63.25 | 63.20 | 67.50 |
| | *(5.01) | (2.40) | (1.65) | (1.33) | (0.99) | (4.01) | (4.91) |
| | +(2.89) | (1.38) | (0.95) | (0.77) | (0.57) | (2.32) | (2.84) |
| (XVIB) | 13.98 | 32.94 | 44.29 | 51.40 | 56.34 | 62.55 | 66.44 |
| | (5.00) | (4.06) | (4.25) | (5.56) | (7.16) | (8.66) | (10.26) |
| | (2.89) | (2.34) | (2.46) | (3.21) | (4.13) | (5.00) | (5.92) |
| (XXXIA) | 3.56 | 12.52 | 18.25 | 24.10 | 28.62 | 33.63 | 35.89 |
| | (2.52) | (2.72) | (3.48) | (3.59) | (3.69) | (3.97) | (5.26) |
| | (1.46) | (1.57) | (2.01) | (2.07) | (2.13) | (2.29) | (3.04) |
| (XXXIB) | 13.56 | 31.40 | 42.13 | 51.00 | 57.23 | 60.60 | 62.93 |
| | (1.64) | (5.51) | (6.99) | (9.15) | (9.63) | (9.70) | (6.12) |
| | (0.95) | (3.18) | (4.04) | (5.28) | (5.56) | (5.60) | (3.53) |

(*standard deviation; +standard error of the mean)

Table III below shows a direct comparison between the level of each $^{99m}$Tc complex excreted into the bladder versus that of $^{131}$I-OIH at 35 minutes after injection.

TABLE III

Comparison of % total dose in bladder at 35 minutes Versus $^{131}$I-OIH

| Compound | $^{99m}$Tc | Average (± s.d) | $^{131}$I | Average (± s.d) | % $\frac{^{99m}Tc}{^{131}I}$ (± s.d.) |
|---|---|---|---|---|---|
| XVI A | 66.64 | 67.50 | 73.14 | 73.60 | 91.71 |
|  | 72.79 | (4.91) | 77.31 | (3.48) | (2.29) |
|  | 63.08 |  | 70.39 |  |  |
| XVI B | 54.63 | 66.44 | 61.75 | 72.02 | 92.25 |
|  | 73.12 | (10.26) | 77.21 | (8.89) | (3.20) |
|  | 71.57 |  | 77.10 |  |  |
| XXXI A | 41.57 | 35.89 | 74.35 | 76.69 | 46.80 |
|  | 31.19 | (5.6) | 82.53 | (5.09) | (9.06) |
|  | 34.90 |  | 73.20 |  |  |
| XXXI B | 69.76 | 62.93 | 87.52 | 80.87 | 77.80 |
|  | 61.09 | (6.12) | 75.71 | (6.04) | (4.19) |
|  | 57.93 |  | 79.39 |  |  |

These data show clearly that all four $^{99m}$Tc- fractions are excreted rapidly in the urine at rates which are comparable to those seen with the existing radiopharmaceutical $^{131}$I-OIH. The final column in Table III also indicates the importance of stereo-chemical factors: the diastereomers isolated as (XVIA) and (XVIB) show comparable rates of excretion to each other and to OIH, whereas a significant difference exists between (XXXIA) and (XXXIB).

The most significant results from these experiments is, therefore, that the pharmacokinetic behavior of the diastereomers (XVIA) and (XVIB) are identical. It can be concluded that a satisfactory renal imaging agent can be obtained with a mixture of the two fractions, i.e. with the product of synthesis, and that chromatographic purification before injection is not necessary. For routine clinical use this is an obvious advantage.

EXAMPLE 18

Biodistribution in Mice of Comoounds (XVIA) and (XVIB)

The diastereomers (XVIA) and (XVIB) were synthesized and then isolated by high pressure liquid chromatography as described previously, and their biodistributions obtained in groups in six Swiss Webster albino male mice. The animals were injected with 0.1 ml (0.5 μCi) of the preparation of Example 13, with propylene glycol as cosolvent. The comparative purposes, 0.2 Ci of $^{131}$I-OIH was added to the $^{99m}$Tc samples and coinjected. The mice were then placed in metabolic cages to collect urine. At 10 and 120 minutes after injection, the penis was ligated, the mice killed with chloroform vapor, and the organs disected. Counting was performed in a dual-channel gamma scintillation counter, with alloance being made in subsequent $^{99m}$Tc calculations for cross-over from the higher energy emissions from $^{131}$I.

The % total dose injected appearing in several major organs at the two time points for the $^{99m}$Tc complexes (XVIA) and (XVIB) are shown in Tables IV and V, respectively, together with the corresponding values obtained for the coinjected $^{131}$I-OIH.

TABLE IV

Biodistribution of XVI A and $^{131}$I-OIH in mice (% total dose per organ, ± s.d.).

| | XVI A | | $^{131}$I-OIH | |
|---|---|---|---|---|
| Organ | 10' | 120' | 10' | 120' |
| Blood | 2.24 ± 0.33 | 0.05 ± 0.01 | 2.80 ± 0.24 | 0.22 ± 0.04 |
| Kidneys | 3.19 ± 0.41 | 0.11 ± 0.04 | 2.18 ± 0.29 | 0.01 ± 0.06 |
| Liver | 1.39 ± 0.31 | 0.19 ± 0.03 | 1.36 ± 0.24 | 0.14 ± 0.03 |
| Stomach | 0.10 ± 0.01 | 0.21 ± 0.47 | 0.36 ± 0.10 | 0.60 ± 0.19 |
| Intestine | 1.07 ± 0.20 | 0.99 ± 0.59 | 1.15 ± 0.23 | 0.45 ± 0.19 |
| Urine | 65.01 ± 9.7 | 89.87 ± 2.70 | 64.80 ± 7.31 | 89.86 ± 3.03 |

TABLE V

Biodistribution of XVI B and $^{131}$I-OIH in mice (% total dose per organ ± s.d.).

| | XVI B | | $^{131}$I-OIH | |
|---|---|---|---|---|
| Organ | 10' | 120' | 10' | 120' |
| Blood | 1.47 ± 0.72 | 0.13 ± 0.10 | 2.11 ± 0.62 | 0.19 ± 0.08 |
| Kidneys | 4.41 ± 3.6 | 0.08 ± 0.07 | 3.09 ± 3.36 | 0.05 ± 0.04 |
| Liver | 0.79 ± 0.49 | 0.11 ± 0.06 | 1.20 ± 0.41 | 0.10 ± 0.04 |
| Stomach | 0.06 ± 0.03 | 0.07 ± 0.12 | 0.42 ± 0.63 | 0.71 ± 0.27 |
| Intestine | 0.48 ± 0.18 | 0.40 ± 0.17 | 0.91 ± 0.27 | 0.24 ± 0.04 |
| Urine | 79.32 ± 5.1 | 91.47 ± 1.1 | 78.86 ± 5.1 | 93.25 ± 0.89 |

The results in these tables show that in this specia both (XVIA) and (XVIB) are cleared rapidly into the urine at comparable rates to each other and to the radiopharmaceutical $^{131}$I-OIH.

The invention has been described in detail with reference to the preferred embodiments thereof. However, it will be appreciated that those skilled in the art, upon consideration of this disclosure may make modifications and improvements within the spirit and scope of this invention.

What is claimed is:

1. Compounds having the structural formula:

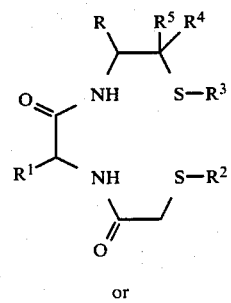

or

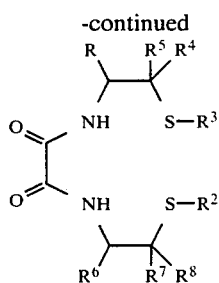

II wherein R and $R^6$ are each selected from hydrogen; unsubstituted lower alkyl; substituted lower alkyl having each of its substituents selected from the group consisting of halide, hydroxy, carboxylic acid or carboxamide; or —$COR^9$;

wherein $R^9$ is selected from hydroxy; unsubstituted lower alkoxy or substituted lower alkoxy having each of its substitutents selected from the group consisting of halide, hydroxy, carboxylic acid or carboxamide; unsubstituted amino or substituted amino having each of its substitutents chosen from the group consisting of lower alkyl or substituted lower alkyl having each of its substitutents selected from the group consisting of halide, hydroxy, carboxylic acid and carboxamide; an ammonium group or substituted ammonium group with a pharmacologically suitable anion; glycine ester or an activated leaving group;

$R^1$ is selected from hydrogen, unsubstituted lower alkyl or substituted lower alkyl having each of its substituents selected from the group consisting of halide, hydroxy, carboxylic acid or carboxamide;

$R^2$ and $R^3$ are each selected from hydrogen or a thiol protecting group; and Rhu 4, $R^5$, $R^7$ and $R^8$ are each selected from hydrogen or lower alkyl;

and salts thereof.

2. A technetium complex having the structural formula:

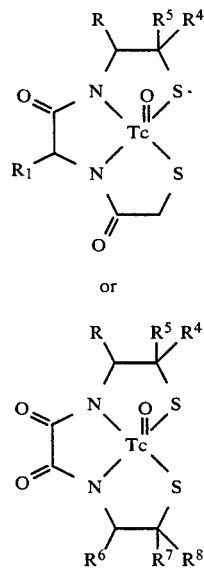

wherein R and $R^6$ are each selected from hydrogen; unsubstituted lower alkyl; substituted lower alkyl having each of its substituents selected from the group consisting of halide, hydroxy, carboxylic acid or carboxamide; or —$COR^9$ where $R^9$ is selected from hydroxy; unsubstituted lower alkoxy, or substituted lower alkoxy having each of its substituents selected from the group consisting of halide, hydroxy, carboxylic acid or carboxamide; unsubstituted amino or substituted amino having each of its substituents chosen from the group consisting of lower alkyl or substituted lower alkyl having each of its substitutents selected from the group consisting of halide, hydroxy, carboxylic acid and carboxamide; and ammonium group or substituted ammonium group with a pharmacologically suitable anion; glycine ester or an activated leaving group;

$R^1$ is selected from hydrogen, unsubstituted lower alkyl, or substituted lower alkyl having each of its substituents selected from the group consisting of halide, hydroxy, carboxylic acid or carboxamide; and $R^4$, $R^5$, $R^7$ and $R^8$ are each selected from hydrogen or lower alkyl;

and salts thereof.

3. Compounds having the structural formula:

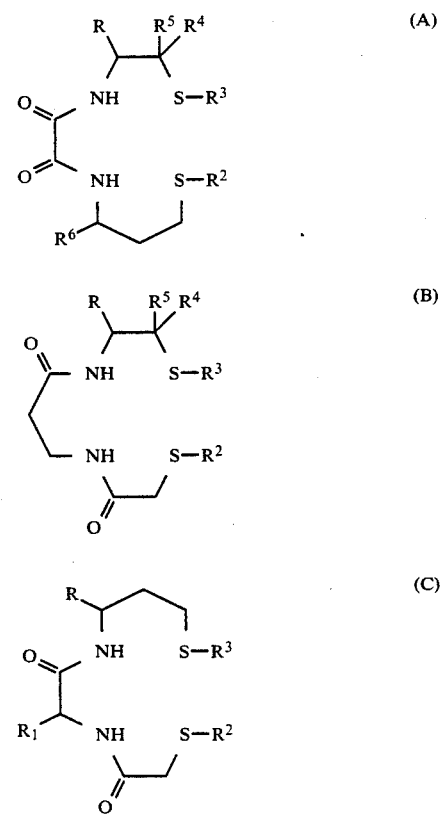

or

-continued

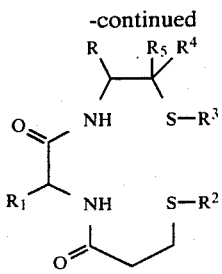

(D)

wherein R and $R^6$ are each selected from hydrogen; unsubstituted lower alkyl; substituted lower alkyl having each of its substituents selected from the group consisting of halide, hydroxy, carboxylic acid or carboxamide; or —$COR^9$
where $R^9$ is selected from hydroxy; unsubstituted lower alkoxy, or substituted lower alkoxy having each of its substituents selected from the group consisting of halide, hydroxy, carboxylic acid or carboxamide; unsubstituted amino or substituted amino having each of its substituents chosen from the group consisting of lower alkyl or substituted lower alkyl having each of its substituents selected from the group consisting of halide, hydroxy, carboxylic acid and carboxamide; an ammonium group or substituted ammonium group with a pharmacologically suitable anion; glycine ester or an activated leaving group;
$R^1$ is selected from hydrogen, unsubstituted lower alkyl or substituted lower alkyl having each of its substituents selected from the group consisting of halide, hydroxy, carboxylic acid or carboxamide;
$R^2$ and $R^3$ are each selected from hydrogen or a thiol protecting group;
$R^4$ and $R^5$ are each selected from hydrogen or lower alykl;
and salts thereof;
with the exception that when said compound has structural formula (C), $R^9$ is not an amino group.

4. A complex formed by reacting said compound of claim 1 with technetium in the presence of a reducing agent.

5. The complex of claim 4 where said reducing agent is a dithionite group, a stannous ion or a ferrous ion.

6. A compound of claim 1 wherein $R^9$ is selected from halide, phenoxy, pentachlorophenoxy, N-oxy-succinimide, and mercapto groups.

7. A compound of claim 1 wherein $R^2$ and $R^3$ are each independently a group selected from acetamidomethyl, lower alkylaminocarbonyl, lower alkanoylaminomethyl, aroylaminomethyl, t-butyl, arylmethyl, aroyl, aryloxycarbonyl, and lower alkoxycarbonyl.

8. A compound of claim 7 wherein $R^2$ and $R^3$ are groups selected from acetamidomethyl, benzoyl, diphenylmethyl, ethylaminocarbonyl, t-butyl, and trityl.

9. A compound of claim 8 wherein both $R^2$ and $R^3$ are acetamidomethyl.

10. A complex of claim 2 wherein $R^9$ is selected from halide, phenoxy, pentachlorophenoxy, N-oxy-succinimido, and mercapto groups.

11. A kit for preparing a radiopharmaceutical preparation comprising a sealed vial containing a predetermined quantity of a compound of claim 1 and a sufficient amount of reducing agent to label said compound with technetium.

12. The kit of claim 11 wherein $R^9$ is selected from halide, phenoxy, pentachlorophenoxy, N-oxy-succinimido, and mercapto groups.

13. The kit of claim 11 wherein $R^2$ and $R^3$ are each independently a group selected from lower acetamidomethyl, alkylaminocarbonyl, lower alkanoylaminomethyl, aroylaminomethyl, t-butyl, arylmethyl, aroyl, aryloxycarbonyl, and lower alkoxycarbonyl.

14. The kit of claim 13 wherein $R^2$ and $R^3$ are groups selected from acetamidomethyl, benzoyl, diphenylmethyl, ethylaminocarbonyl, t-butyl, and trityl.

15. The kit of claim 14 wherein both $R^2$ and $R^3$ are acetamidomethyl.

16. The kit of claim 11 wherein said reducing agent is a dithionite group, a stannous ion, or a ferrous ion.

17. A kit for preparing a radiopharmaceutical preparation comprising a sterilized, sealed vial comprising a lyophilized admixture of a reducing agent for technetium and a bisamido-bisthio compound capable of forming a 5 coordinate oxotechnetium complex in an aqueous solution having a pH in the range of about 5 to 8.

18. The kit of claim 17 wherein said reducing agent is selected from stannous ion, a dithionite moiety, and ferrous ion.

19. The kit of claim 18 wherein said reducing agent is stannous chloride.

20. The kit of claim 17 wherein said bisamido-bisthio compound is selected from:
N-(2-mercaptoethyl)-(2-mercaptoacetyl)glycinamide;
N-[2-(benzoylthio)ethyl]-(2-benzoylthioacetyl)glycinamide;
N-[2-(acetamidomethylthio)ethyl]-(2-acetamidomethylthioacetyl)glycinamide;
(2-mercaptoacetyl)glycyl-cysteine methyl ester;
(2-benzoylthioacetyl)glycyl-(S-benzoyl)cysteine methyl ester;
[2-(acetamidomethylthio)acetyl]glycyl-(S-acetamidomethyl)cysteine methyl ester;
(2-mercaptoacetyl)glycyl-cysteine;
(2-benzoylthioacetyl)glycyl-(S-benzoyl)cysteine;
2-(acetamidomethylthio)acetyl]glycyl-(S-acetamidomethyl)cysteine;
(2-mercaptoacetyl)glycyl-cysteinyl-glycine methyl ester;
(2-benzoylthioacetyl)glycyl-(S-benzoyl)cysteinyl-glycine methyl ester;
[2-(acetamidomethylthio)acetyl]glycyl-(S-acetamidomethyl)cysteinyl-glycine methyl ester;
N-(2-mercaptoethyl)-N'-(1-carbomethoxy-2-mercaptoethyl)oxamide;
N-[2-(benzoylthio)ethyl]-N'-[1-carbomethoxy-2-(benzoylthio)ethyl]oxamide;
N-[2-(acetamidomethylthio)ethyl]-N'-[1-carbomethoxy-2-(acetamidomethylthio)ethyl]oxamide;
N,N'-bis(2-mercaptoethyl)oxamide;
N,N'-bis[2-(benzoylthio)ethyl]oxamide;
N,N'-bis[2-(acetamidomethylthio)ethyl]oxamide;
(R,R)N,N'-bis(1-carbomethoxy-2-mercaptoethyl)oxamide;
(R,R)N,N'-bis[1-carbomethoxy-2-(benzoylthio)ethyl]oxamide; and
(R,R)N,N'-bis[1-carbomethoxy-2-(acetamidomethylthio)ethyl]oxamide.

21. The kit of claim 17 wherein said bisamido-bisthio compound has a hydrophilic thiol protecting group.

22. The kit of claim 17 wherein said bisamido-bisthio compound has an acetamidomethyl thiol protecting group.

23. The kit of claim 17 wherein said bisamido-bisthio compound has two acetamidomethyl thiol protecting groups.

24. The kit of claim 17 wherein the sulfur atom at each end of said compound has a hydrophilic thiol protecting group.

25. The kit of claim 24 wherein said thiol group is acetamidomethyl.

26. A method for diagnosing kidney disfunction in a mammal comprising injecting into said mammal a technetium complex in accord with claim 2 in a suitable pharmacological carrier; and scanning the renal system of said mammal using radioscintigraphic imaging apparatus.

27. A complex formed by reacting said compound of claim 3 with technetium in the presence of a reducing agent.

28. A compound in accord with claim 3 wherein $R^2$ and $R^3$ are groups selected from acetamidomethyl, benzoyl, diphenylrethyl, ethylaminocarbonyl, t-butyl, and trityl.

29. The compound of claim 28 wherein $R^2$ and $R^3$ are acetamidomethyl.

30. A kit for preparing a radiopharmaceutical preparation comprising a sealed vial containing predetermined quantity of a compound of claim 26 and a sufficient amount of reducing agent to label said compound with technetium.

31. The kit of claim 30 wherein said reducing agent is a stannous ion.

32. The kit of claim 30 wherein said compound has acetamidomethyl thiol protecting groups.

33. The kit of claim 30 wherein said comound and said reducing agent are lyophilized in a sterile vial and said compound is capable of forming a 5 coordinate oxotechnetium complex in an aqueous solution having a pH in the range of about 5 to 8.

34. (2-Benzoylthioacetyl)-glycyl-(S-benzoyl)cysteine methyl ester.

35. A kit for preparing a radiopharmaceutical preparation comprising a sealed vial containing predetermined quantity of a compound of claim 34 and a sufficient amount of reducing agent to label said compound with technetium.

36. (2-Acetamidomethylthio)acetyl-glycyl-(S-acetamidomethyl)cysteine methyl ester.

37. A kit for preparing a radiopharmaceutical preparation comprising a sealed vial containing predetermined quantity of a compound of claim 36 and a sufficient amount of reducing agent to label said compound with technetium.

38. (2-Acetamidomethylthio)acetyl-glycyl-(S-acetamidomethyl)cysteine.

39. A kit for preparing a radiopharmaceutical preparation comprising a sealed vial containing predetermined quantity of a compound of claim 38 and a sufficient amount of reducing agent to label said compound with technetium.

40. (2-Benzoylthioacetyl)glycyl-(S-benzoyl)cysteinyl-glycine methyl ester.

41. A kit for preparing a radiopharmaceutical preparation comprising a sealed vial containing predetermined quantity of a compound of claim 40 and a sufficient amount of reducing agent to label said compound with technetium.

42. N-[(2-benzoylthio)ethyl]-N-'[1-carbomethoxy-(2-benzoylthio)ethyl)-oxamide.

43. A kit for preparing a radiopharmaceutical preparation comprising a sealed vial containing predetermined quantity of a compound of claim 42 and a sufficient amount of reducing agent to label said compound with technetium.

44. N,N'-bis(1-carbomethoxy-2-benzoylthioethyl)oxamide.

45. A kit for preparing a radiopharmaceutical preparation comprising a sealed vial containing predetermined quantity of a compound of claim 44 and a sufficient amount of reducing agent to label said compound with technetium.

* * * * *

UNITED STATES PATENT AND TRADEMARK OFFICE
CERTIFICATE OF CORRECTION

PATENT NO. : 4,673,562

DATED : June 16, 1987

INVENTOR(S) : ALAN DAVISON ET AL.

It is certified that error appears in the above-identified patent and that said Letters Patent is hereby corrected as shown below:

In the front of the patent, an additional assignee has been left out. It should read: The Children's Medical Center Corporation, Boston; Massachusetts Institute of Technology, Cambridge; and President and Fellows of Harvard College, Cambridge, all of Mass.;

2. Under "REFERENCES CITED", "4,434,151 BYRNE" should be included;

3. Under "OTHER PUBLICATIONS", line 7 of page 2 "Potential" is misspelled;

Col. 9, line 2, "are" is misspelled;

Col. 12, line 28, "gave" is misspelled;

Col. 12, line 32, "acetyl1]" should be --acetyl]--;

Col. 12, line 58, "CHCL$_1$3" should be --CHC$l_3$--;

UNITED STATES PATENT AND TRADEMARK OFFICE
CERTIFICATE OF CORRECTION

PATENT NO. : 4,673,562

DATED : JUNE 16, 1987

INVENTOR(S) : ALAN DAVISON ET AL.

It is certified that error appears in the above-identified patent and that said Letters Patent is hereby corrected as shown below:

Col. 13, lines 15-65 should read:

A.

B. 

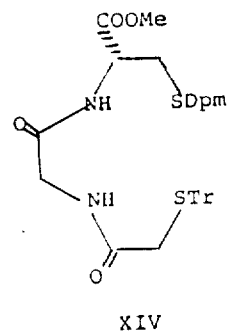

FORMULA CONTINUED ON NEXT PAGE

UNITED STATES PATENT AND TRADEMARK OFFICE
CERTIFICATE OF CORRECTION

PATENT NO. : 4,673,562
DATED : JUNE 16, 1987
INVENTOR(S) : ALAN DAVISON ET AL.

It is certified that error appears in the above-identified patent and that said Letters Patent is hereby corrected as shown below:

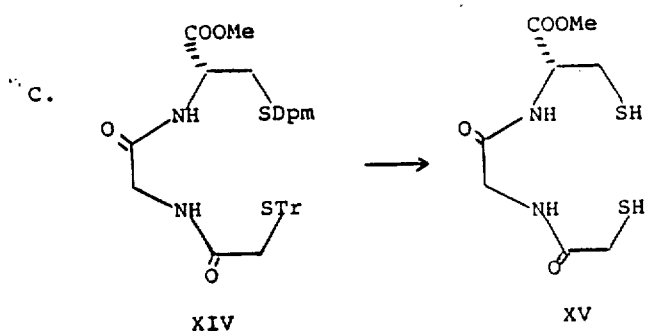

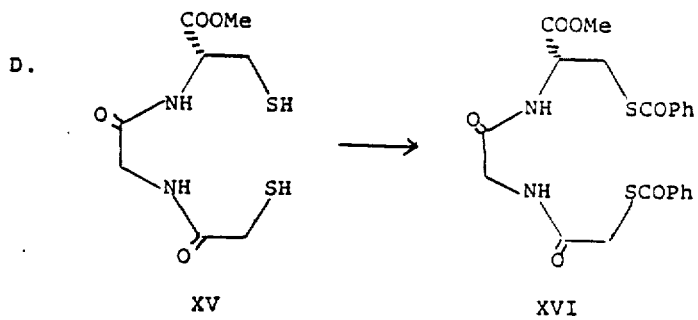

UNITED STATES PATENT AND TRADEMARK OFFICE
CERTIFICATE OF CORRECTION

PATENT NO. : 4,673,562
DATED : JUNE 16, 1987
INVENTOR(S) : ALAN DAVISON ET AL.

It is certified that error appears in the above-identified patent and that said Letters Patent is hereby corrected as shown below:

Col. 14, line 25, "ester" is misspelled;

Col. 15, lines 6-17 should read:

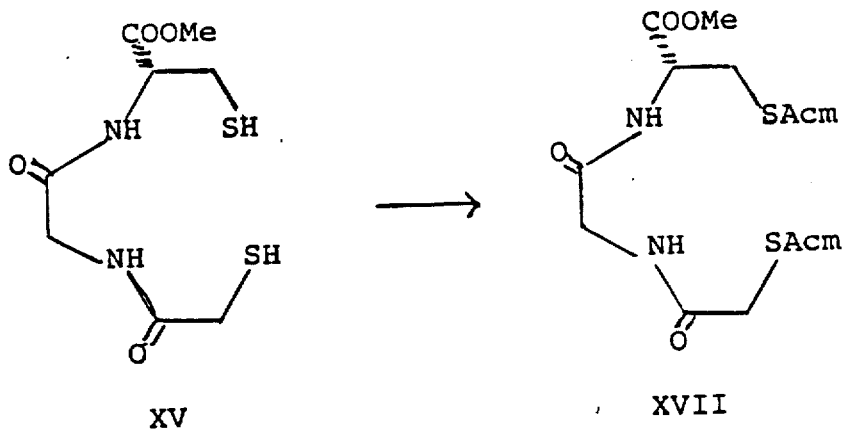

UNITED STATES PATENT AND TRADEMARK OFFICE
CERTIFICATE OF CORRECTION

PATENT NO. : 4,673,562
DATED : JUNE 16, 1987
INVENTOR(S) : ALAN DAVISON ET AL.

It is certified that error appears in the above-identified patent and that said Letters Patent is hereby corrected as shown below:

Col. 16, line 30, add a semicolon after "hygroscopic";

Col. 16, lines 60-65 should read:

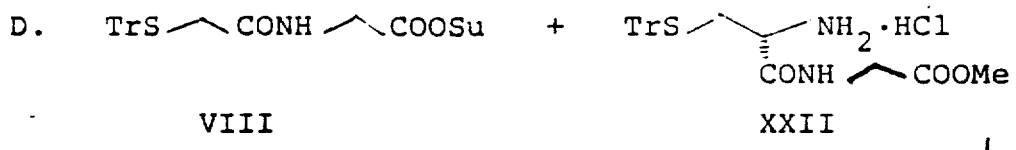

Col. 18, line 57, "(CH₃OH)" should be --(CH₃OH)--;

Col. 18, line 63, "ethylloxamide" should be --ethyloxamide--;

Col. 20, line 17, "ethyl-9 oxamic acid" should be --ethyloxamic acid--;

Col. 20, line 28, "NaCl," has not been printed clearly;

Col. 20, line 30, "(89%)" has not been printed clearly;

UNITED STATES PATENT AND TRADEMARK OFFICE
CERTIFICATE OF CORRECTION

PATENT NO. : 4,673,562
DATED : JUNE 16, 1987
INVENTOR(S) : ALAN DAVISON ET AL.

It is certified that error appears in the above-identified patent and that said Letters Patent is hereby corrected as shown below:

Col. 20, line 31, "amount" has not been printed clearly;

Col. 20, line 66, "vacuo" is misspelled;

Col. 21, line 46, "remained" is misspelled;

Col. 22, lines 10-15, should read:

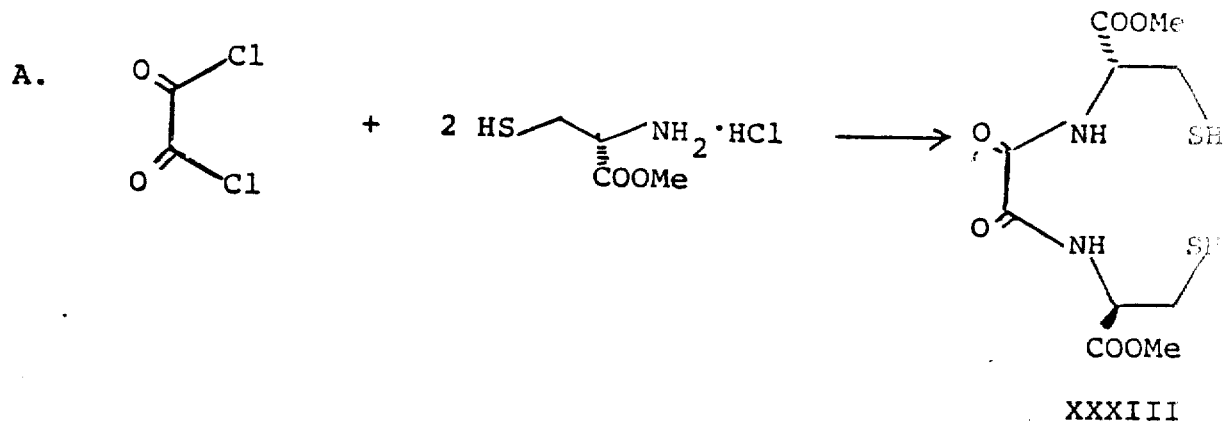

UNITED STATES PATENT AND TRADEMARK OFFICE
CERTIFICATE OF CORRECTION

PATENT NO. : 4,673,562
DATED : JUNE 16, 1987
INVENTOR(S) : ALAN DAVISON ET AL.

It is certified that error appears in the above-identified patent and that said Letters Patent is hereby corrected as shown below:

Col. 22, line 37, "(2mercaptoethyl)oxamide" should be --(2-mercaptoethyl)oxamide--;

Col. 22, line 58, "CHClphd" should be --CHCl$_3$/hexanes--;

Col. 23, lines 29-45 should read:

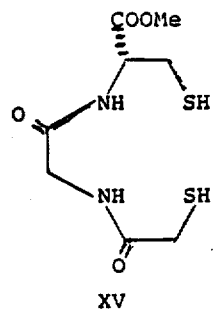

XV

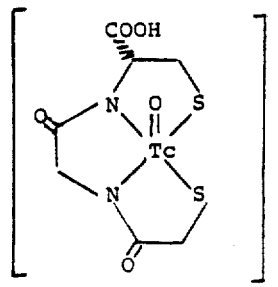

XXXVI

UNITED STATES PATENT AND TRADEMARK OFFICE
CERTIFICATE OF CORRECTION

PATENT NO. : 4,673,562

DATED : JUNE 16, 1987

INVENTOR(S) : ALAN DAVISON ET AL.

It is certified that error appears in the above–identified patent and that said Letters Patent is hereby corrected as shown below:

Col. 26, line 54, "Ligand" is misspelled;

Col. 26, line 68, "minute" should be --minutes--;

Col. 27, line 62, "ethyl)" should be --ethyl]--;

Col. 28, line 36, "values" is misspelled;

Col. 29, line 13, under the column titled "Average", "(5.6)" should be --(5.26)--;

Col. 30, line 9, "allowance" is misspelled;

UNITED STATES PATENT AND TRADEMARK OFFICE
CERTIFICATE OF CORRECTION

PATENT NO. : 4,673,562

DATED : JUNE 16, 1987

INVENTOR(S) : ALAN DAVISON ET AL.

It is certified that error appears in the above-identified patent and that said Letters Patent is hereby corrected as shown below:

Col. 31, line 37, "Rhu4" should be --$R^4$--;

Col. 34, line 43, "2-(acetamidomethylthio)..." should be --[2-(acetamidomethylthio)....--;

Col. 35, line 25, "diphenylmethyl" is misspelled;

Col. 36, line 30, "ethyl)-oxamide." should be --ethyl]-oxamide.--.

Signed and Sealed this

Twenty-first Day of January, 1992

Attest:

HARRY F. MANBECK, JR.

*Attesting Officer*  *Commissioner of Patents and Trademarks*